(12) United States Patent
Falotico et al.

(10) Patent No.: US 7,229,473 B2
(45) Date of Patent: *Jun. 12, 2007

(54) LOCAL DELIVERY OF RAPAMYCIN FOR TREATMENT OF PROLIFERATIVE SEQUELAE ASSOCIATED WITH PTCA PROCEDURES, INCLUDING DELIVERY USING A MODIFIED STENT

(75) Inventors: Robert Falotico, Bell Mead, NJ (US); Gerard H. Llanos, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/466,983

(22) Filed: Aug. 24, 2006

(65) Prior Publication Data

US 2006/0282160 A1    Dec. 14, 2006

Related U.S. Application Data

(63) Continuation of application No. 10/951,385, filed on Sep. 28, 2004, which is a continuation of application No. 10/408,328, filed on Apr. 7, 2003, now Pat. No. 6,808,536, which is a continuation of application No. 09/874,117, filed on Jun. 4, 2001, now Pat. No. 6,585,764, which is a continuation of application No. 09/061,586, filed on Apr. 16, 1998, now Pat. No. 6,273,913.

(60) Provisional application No. 60/044,692, filed on Apr. 18, 1997.

(51) Int. Cl.
*A61F 2/06* (2006.01)

(52) U.S. Cl. .................................................. 623/1.42
(58) Field of Classification Search ....... 623/1.42–1.48
See application file for complete search history.

(56) References Cited

U.S. PATENT DOCUMENTS

| | | | |
|---|---|---|---|
| 861,659 A | 7/1907 | Johnston | 464/147 |
| 3,051,677 A | 8/1962 | Rexford | 522/156 |
| 3,279,996 A | 10/1966 | Long et al. | 424/424 |
| 3,526,005 A | 9/1970 | Bokros | 623/11.11 |
| 3,599,641 A | 8/1971 | Sheridan | 604/256 |
| 3,657,744 A | 4/1972 | Ersek | 128/898 |
| 3,744,596 A | 7/1973 | Sander | 188/203 |
| 3,779,805 A | 12/1973 | Alsbeg | 427/105 |

(Continued)

FOREIGN PATENT DOCUMENTS

DE        3205942 A1    9/1983

(Continued)

OTHER PUBLICATIONS

U.S. Appl. No. 07/819,314, filed Jan. 9, 1992, Morris.

(Continued)

*Primary Examiner*—Suzette Gherbi
(74) *Attorney, Agent, or Firm*—Woodcock Washburn LLP (57) ABSTRACT

Methods of preparing intravascular stents with a polymeric coating containing macrocyclic lactone (such as rapamycin or its analogs), stents and stent grafts with such coatings, and methods of treating a coronary artery with such devices. The macrocyclic lactone-based polymeric coating facilitates the performance of such devices in inhibiting restenosis.

5 Claims, 2 Drawing Sheets

U.S. PATENT DOCUMENTS

| | | | |
|---|---|---|---|
| 3,929,992 A | 12/1975 | Sehgal et al. | 424/122 |
| 3,932,627 A | 1/1976 | Margraf | 514/56 |
| 3,948,254 A | 4/1976 | Zaffaroni | 128/833 |
| 3,952,334 A | 4/1976 | Bokros et al. | 623/11.11 |
| 3,968,800 A | 7/1976 | Vilasi | 606/198 |
| 4,069,307 A | 1/1978 | Higuchi et al. | 424/432 |
| 4,076,285 A | 2/1978 | Martinez | 285/332 |
| 4,292,965 A | 10/1981 | Nash et al. | 128/833 |
| 4,299,226 A | 11/1981 | Banka | 604/509 |
| 4,300,244 A | 11/1981 | Bokros | 623/1.13 |
| 4,312,920 A | 1/1982 | Pierce et al. | 428/425.5 |
| 4,321,711 A | 3/1982 | Mano | 623/1.43 |
| 4,323,071 A | 4/1982 | Simpson et al. | 606/194 |
| 4,390,599 A | 6/1983 | Broyles | 428/597 |
| 4,413,359 A | 11/1983 | Akiyama et al. | 623/23.72 |
| 4,423,183 A | 12/1983 | Close | 524/546 |
| 4,441,216 A | 4/1984 | Ionescu et al. | 623/2.19 |
| 4,503,569 A | 3/1985 | Dotter | 623/1.19 |
| 4,512,338 A | 4/1985 | Balko et al. | 606/108 |
| 4,550,447 A | 11/1985 | Seiler, Jr. et al. | 623/1.32 |
| 4,553,545 A | 11/1985 | Maass et al. | 606/198 |
| 4,560,374 A | 12/1985 | Hammerslag | 604/509 |
| 4,562,596 A | 1/1986 | Kornberg | 623/1.32 |
| 4,565,740 A | 1/1986 | Golander et al. | 428/409 |
| 4,580,568 A | 4/1986 | Gianturco | 606/198 |
| 4,613,665 A | 9/1986 | Larm | 536/20 |
| 4,642,111 A | 2/1987 | Sakamoto et al. | 424/492 |
| 4,655,771 A | 4/1987 | Wallsten | 623/1.22 |
| 4,656,083 A | 4/1987 | Hoffman et al. | 442/123 |
| 4,676,241 A | 6/1987 | Webb et al. | 128/207.14 |
| 4,678,466 A | 7/1987 | Rosenwald | 424/427 |
| 4,687,482 A | 8/1987 | Hanson | 623/1.49 |
| 4,689,046 A | 8/1987 | Bokros | 623/2.31 |
| 4,731,054 A | 3/1988 | Billeter et al. | 604/93.01 |
| 4,733,665 A | 3/1988 | Palmaz | 606/108 |
| 4,739,762 A | 4/1988 | Palmaz | 623/1.11 |
| 4,740,207 A | 4/1988 | Kreamer | 623/1.15 |
| 4,749,585 A | 6/1988 | Greco et al. | 428/422 |
| 4,753,652 A | 6/1988 | Langer et al. | 623/1.42 |
| 4,760,849 A | 8/1988 | Kropf | 606/191 |
| 4,768,507 A | 9/1988 | Fischell et al. | 623/1.11 |
| 4,776,337 A | 10/1988 | Palmaz | 623/1.11 |
| 4,786,500 A | 11/1988 | Wong | 424/422 |
| 4,787,899 A | 11/1988 | Lazarus | 623/1.11 |
| 4,800,882 A | 1/1989 | Gianturco | 606/194 |
| 4,810,784 A | 3/1989 | Larm | 536/20 |
| 4,856,516 A | 8/1989 | Hillstead | 606/194 |
| 4,871,357 A | 10/1989 | Hsu et al. | 604/266 |
| 4,872,867 A | 10/1989 | Joh | 604/269 |
| 4,876,109 A | 10/1989 | Mayer et al. | 604/269 |
| 4,886,062 A | 12/1989 | Wiktor | 606/194 |
| 4,907,336 A | 3/1990 | Gianturco | 29/515 |
| 4,916,193 A | 4/1990 | Tang et al. | 525/413 |
| 4,954,126 A | 9/1990 | Wallsten | 600/36 |
| 4,969,458 A | 11/1990 | Wiktor | 623/1.11 |
| 4,990,131 A | 2/1991 | Dardik et al. | 600/36 |
| 4,990,155 A | 2/1991 | Wilkoff | 606/191 |
| 4,994,071 A | 2/1991 | MacGregor | 606/194 |
| 4,994,298 A | 2/1991 | Yasuda | 427/490 |
| 4,998,923 A | 3/1991 | Samson et al. | 606/194 |
| 5,015,253 A | 5/1991 | MacGregor | 623/1.15 |
| 5,019,090 A | 5/1991 | Pinchuk | 623/1.15 |
| 5,019,096 A | 5/1991 | Fox, Jr. et al. | 600/36 |
| 5,029,877 A | 7/1991 | Fedeli | 277/354 |
| 5,034,265 A | 7/1991 | Hoffman et al. | 442/126 |
| 5,035,706 A | 7/1991 | Gianturco et al. | 606/198 |
| 5,041,100 A | 8/1991 | Rowland et al. | 604/265 |
| 5,041,126 A | 8/1991 | Gianturco | 623/1.15 |
| 5,047,020 A | 9/1991 | Hsu | 604/266 |
| 5,049,132 A | 9/1991 | Shaffer et al. | 604/101.02 |
| 5,049,403 A | 9/1991 | Larm et al. | 427/2.1 |
| 5,053,048 A | 10/1991 | Pinchuk | 623/1.43 |
| 5,059,166 A | 10/1991 | Fischell et al. | 600/3 |
| 5,061,275 A | 10/1991 | Wallsten et al. | 623/1.22 |
| 5,061,750 A | 10/1991 | Feijen et al. | 525/54.1 |
| 5,064,435 A | 11/1991 | Porter | 623/23.7 |
| 5,092,877 A | 3/1992 | Pinchuk | 128/898 |
| 5,102,417 A | 4/1992 | Palmaz | 606/195 |
| 5,104,404 A | 4/1992 | Wolff | 623/1.16 |
| 5,116,365 A | 5/1992 | Hillstead | 623/1.15 |
| 5,122,154 A | 6/1992 | Rhodes | 623/1.13 |
| 5,131,908 A | 7/1992 | Dardik et al. | 600/36 |
| 5,133,732 A | 7/1992 | Wiktor | 623/1.22 |
| 5,134,192 A | 7/1992 | Feijen et al. | 525/54.1 |
| 5,135,536 A | 8/1992 | Hillstead | 606/195 |
| 5,163,952 A | 11/1992 | Froix | 623/1.18 |
| 5,163,958 A | 11/1992 | Pinchuk | 623/23.49 |
| 5,171,217 A | 12/1992 | March et al. | 604/507 |
| 5,171,262 A | 12/1992 | MacGregor | 623/1.15 |
| 5,176,660 A | 1/1993 | Truckai | 604/527 |
| 5,176,972 A | 1/1993 | Bloom et al. | 430/14 |
| 5,178,618 A | 1/1993 | Kandarpa | 606/28 |
| 5,180,366 A | 1/1993 | Woods | 604/96.01 |
| 5,182,317 A | 1/1993 | Winters et al. | 523/112 |
| 5,185,408 A | 2/1993 | Tang et al. | 525/415 |
| 5,192,307 A | 3/1993 | Wall | 623/1.2 |
| 5,195,984 A | 3/1993 | Schatz | 623/1.2 |
| 5,213,576 A | 5/1993 | Abiuso et al. | 604/103.01 |
| 5,213,898 A | 5/1993 | Larm et al. | 428/422 |
| 5,217,483 A | 6/1993 | Tower | 623/1.15 |
| 5,222,971 A | 6/1993 | Willard et al. | 606/198 |
| 5,226,913 A | 7/1993 | Pinchuk | 140/71 R |
| 5,234,456 A | 8/1993 | Silvestrini | 623/1.2 |
| 5,246,445 A | 9/1993 | Yachia et al. | 623/1.2 |
| 5,258,020 A | 11/1993 | Froix | 128/898 |
| 5,258,021 A | 11/1993 | Duran | 623/2.3 |
| 5,262,451 A | 11/1993 | Winters et al. | 523/112 |
| 5,266,073 A | 11/1993 | Wall | 623/1.2 |
| 5,272,012 A | 12/1993 | Opolski | 428/423.1 |
| 4,733,665 A | 1/1994 | Palmaz | 606/108 |
| 5,275,622 A | 1/1994 | Lazarus et al. | 623/1.11 |
| 5,282,823 A | 2/1994 | Schwartz et al. | 623/1.22 |
| 5,282,824 A | 2/1994 | Gianturco | 623/1.13 |
| 5,283,257 A | 2/1994 | Gregory et al. | 514/458 |
| 5,288,711 A | 2/1994 | Mitchell et al. | 424/122 |
| 5,290,305 A | 3/1994 | Inoue | 623/1.2 |
| 5,292,331 A | 3/1994 | Boneau | 623/1.16 |
| 5,292,802 A | 3/1994 | Rhee et al. | 525/54.1 |
| 5,304,121 A | 4/1994 | Sahatjian | 604/509 |
| 5,304,200 A | 4/1994 | Spaulding | 623/1.16 |
| 5,306,250 A | 4/1994 | March et al. | 604/104 |
| 5,308,862 A | 5/1994 | Ohlstein | 514/411 |
| 5,308,889 A | 5/1994 | Rhee et al. | 523/113 |
| 5,314,444 A | 5/1994 | Gianturco | 606/195 |
| 5,314,472 A | 5/1994 | Fontaine | 623/1.22 |
| 5,328,471 A | 7/1994 | Slepian | 604/101.03 |
| 5,334,301 A | 8/1994 | Heinke et al. | 204/267 |
| 5,336,518 A | 8/1994 | Narayanan et al. | 427/470 |
| 5,338,770 A | 8/1994 | Winters et al. | 523/112 |
| 5,342,348 A | 8/1994 | Kaplan | 604/891.1 |
| 5,342,387 A | 8/1994 | Summers | 606/198 |
| 5,342,621 A | 8/1994 | Eury | 606/198 |
| 5,354,257 A | 10/1994 | Roubin et al. | 600/7 |
| 5,354,308 A | 10/1994 | Simon et al. | 623/1.15 |
| 5,356,433 A | 10/1994 | Rowland et al. | 424/422 |
| 5,366,504 A | 11/1994 | Andersen et al. | 623/1.5 |
| 5,368,566 A | 11/1994 | Crocker | 604/101.02 |
| 5,370,683 A | 12/1994 | Fontaine | 623/1.22 |
| 5,370,691 A | 12/1994 | Samson | 623/1.22 |
| 5,375,612 A | 12/1994 | Cottenceau et al. | 128/899 |
| 5,376,112 A | 12/1994 | Duran | 623/1.26 |
| 5,378,475 A | 1/1995 | Smith et al. | 424/473 |
| 5,380,299 A | 1/1995 | Fearnot et al. | 604/265 |
| 5,382,261 A | 1/1995 | Palmaz | 606/158 |

| Patent | Date | Inventor | Class |
|---|---|---|---|
| 5,383,853 A | 1/1995 | Jung et al. | 604/103.04 |
| 5,383,928 A | 1/1995 | Scott et al. | 623/1.12 |
| 5,387,235 A | 2/1995 | Chuter | 623/1.11 |
| 5,389,106 A | 2/1995 | Tower | 623/1.15 |
| 5,393,772 A | 2/1995 | Yue et al. | 514/410 |
| 5,395,390 A | 3/1995 | Simon et al. | 623/1.18 |
| 5,397,355 A | 3/1995 | Marin et al. | 623/1.2 |
| 5,399,352 A | 3/1995 | Hanson | 424/423 |
| 5,403,341 A | 4/1995 | Solar | 606/198 |
| 5,405,377 A | 4/1995 | Cragg | 623/1.2 |
| 5,409,696 A | 4/1995 | Narayanan et al. | 424/78.17 |
| 5,411,549 A | 5/1995 | Peters | 623/1.15 |
| 5,415,619 A | 5/1995 | Lee et al. | 600/36 |
| 5,417,969 A | 5/1995 | Hsu et al. | 424/78.27 |
| 5,419,760 A | 5/1995 | Narcisco, Jr. | 604/8 |
| D359,802 S | 6/1995 | Fontaine | D24/155 |
| 5,421,955 A | 6/1995 | Lau et al. | 216/48 |
| 5,423,885 A | 6/1995 | Williams | 623/1.17 |
| 5,429,618 A | 7/1995 | Keogh | 604/266 |
| 5,429,634 A | 7/1995 | Narciso, Jr. | 604/890.1 |
| 5,439,446 A | 8/1995 | Barry | 604/103.01 |
| 5,441,515 A | 8/1995 | Khosravi et al. | 606/194 |
| 5,441,516 A | 8/1995 | Wang et al. | 606/198 |
| 5,441,947 A | 8/1995 | Dodge et al. | 514/179 |
| 5,443,458 A | 8/1995 | Evry | 604/891.1 |
| 5,443,477 A | 8/1995 | Marin et al. | 606/198 |
| 5,443,496 A | 8/1995 | Schwartz et al. | 623/1.16 |
| 5,443,498 A | 8/1995 | Fontaine | 623/1.17 |
| 5,443,500 A | 8/1995 | Sigwart | 623/1.17 |
| 5,447,724 A | 9/1995 | Helmus et al. | 424/426 |
| 5,449,372 A | 9/1995 | Schmaltz et al. | 606/198 |
| 5,449,373 A | 9/1995 | Pinchasik et al. | 606/198 |
| 5,449,382 A | 9/1995 | Dayton | 623/1.15 |
| 5,464,450 A | 11/1995 | Buscemi et al. | 632/1.2 |
| 5,464,540 A | 11/1995 | Friesen et al. | 210/640 |
| 5,464,650 A | 11/1995 | Berg et al. | 427/2.3 |
| 5,474,563 A | 12/1995 | Myler et al. | 606/198 |
| 5,486,357 A | 1/1996 | Narayanan | 424/78.17 |
| 5,496,365 A | 3/1996 | Sgro | 623/1.2 |
| 5,500,013 A | 3/1996 | Buscemi et al. | 623/1.22 |
| 5,510,077 A | 4/1996 | Dinh et al. | 264/485 |
| 5,512,055 A | 4/1996 | Domb et al. | 604/265 |
| 5,516,781 A | 5/1996 | Morris et al. | 514/291 |
| 5,519,042 A | 5/1996 | Morris et al. | 514/378 |
| 5,523,092 A | 6/1996 | Hanson et al. | 424/423 |
| 5,527,354 A | 6/1996 | Fontaine et al. | 623/1.17 |
| 5,545,208 A | 8/1996 | Wolff et al. | 623/1.22 |
| 5,551,954 A | 9/1996 | Buscemi et al. | 623/1.15 |
| 5,554,182 A | 9/1996 | Dinh et al. | 600/36 |
| 5,554,954 A | 9/1996 | Takahashi | 327/546 |
| 5,556,413 A | 9/1996 | Lam | 623/1.2 |
| 5,562,922 A | 10/1996 | Lambert | 424/486 |
| 5,563,146 A | 10/1996 | Morris | 514/291 |
| 5,569,197 A | 10/1996 | Helmus | 604/102.02 |
| 5,569,295 A | 10/1996 | Lam | 606/198 |
| 5,569,462 A | 10/1996 | Martinson et al. | 424/423 |
| 5,569,463 A | 10/1996 | Helmus et al. | 424/426 |
| 5,571,089 A | 11/1996 | Crocker | 604/103.01 |
| 5,571,166 A | 11/1996 | Dinh et al. | 128/898 |
| 5,574,059 A | 11/1996 | Regunathan et al. | 514/397 |
| 5,575,818 A | 11/1996 | Pinchuk | 623/1.15 |
| 5,578,075 A | 11/1996 | Dayton | 623/1.15 |
| 5,580,873 A | 12/1996 | Bianco et al. | 514/263.36 |
| 5,580,874 A | 12/1996 | Bianco et al. | 514/263.36 |
| 5,591,140 A | 1/1997 | Narayanan et al. | 604/269 |
| 5,591,197 A | 1/1997 | Orth et al. | 623/1.16 |
| 5,591,224 A | 1/1997 | Schwartz et al. | 623/1.22 |
| 5,591,227 A | 1/1997 | Dinh et al. | 623/1.22 |
| 5,599,352 A | 2/1997 | Dinh et al. | 128/898 |
| 5,603,722 A | 2/1997 | Phan et al. | 623/1.18 |
| 5,604,283 A | 2/1997 | Wada et al. | 524/236 |
| 5,605,696 A | 2/1997 | Eury et al. | 424/423 |
| 5,607,463 A | 3/1997 | Schwartz et al. | 623/1.44 |
| 5,607,475 A | 3/1997 | Cahalan et al. | 424/423 |
| 5,609,629 A | 3/1997 | Fearnot et al. | 623/1.42 |
| 5,616,608 A | 4/1997 | Kinsella et al. | 514/449 |
| 5,620,984 A | 4/1997 | Bianco et al. | 514/263.36 |
| 5,621,102 A | 4/1997 | Bianco et al. | 544/267 |
| 5,622,975 A | 4/1997 | Singh et al. | 514/324 |
| 5,624,411 A | 4/1997 | Tuch | 604/265 |
| 5,628,785 A | 5/1997 | Schwartz et al. | 128/898 |
| 5,629,077 A | 5/1997 | Turnlund et al. | 623/1.15 |
| 5,629,315 A | 5/1997 | Bianco et al. | 514/263.36 |
| 5,632,763 A | 5/1997 | Glastra | 623/1.15 |
| 5,632,771 A | 5/1997 | Boatman et al. | 623/1.15 |
| 5,632,776 A | 5/1997 | Kurumatani et al. | 424/423 |
| 5,632,840 A | 5/1997 | Campbell | 156/196 |
| 5,635,201 A | 6/1997 | Fabo | 424/443 |
| 5,637,113 A | 6/1997 | Tartaglia et al. | 623/1.42 |
| 5,643,312 A | 7/1997 | Fischell et al. | 623/1.15 |
| 5,643,939 A | 7/1997 | Ohlstein | 514/411 |
| 5,646,160 A | 7/1997 | Morris et al. | 514/291 |
| 5,648,357 A | 7/1997 | Bianco et al. | 514/263.36 |
| 5,649,952 A | 7/1997 | Lam | 623/1.15 |
| 5,649,977 A | 7/1997 | Campbell | 623/1.15 |
| 5,651,174 A | 7/1997 | Schwartz et al. | 29/527.2 |
| 5,652,243 A | 7/1997 | Bianco et al. | 514/263.36 |
| 5,653,747 A | 8/1997 | Dereume | 623/1.54 |
| 5,653,992 A | 8/1997 | Bezwada et al. | 424/426 |
| 5,662,609 A | 9/1997 | Slepian | 604/101.03 |
| 5,665,591 A | 9/1997 | Sonenshein et al. | 435/375 |
| 5,665,728 A | 9/1997 | Morris et al. | 424/122 |
| 5,667,764 A | 9/1997 | Kopia et al. | 424/1.45 |
| 5,669,924 A | 9/1997 | Shaknovich | 623/1.11 |
| 5,670,506 A | 9/1997 | Leigh et al. | 514/141 |
| 5,672,638 A | 9/1997 | Verhoeven et al. | 523/112 |
| 5,674,242 A | 10/1997 | Phan et al. | 606/198 |
| 5,679,400 A | 10/1997 | Tuch | 427/2.14 |
| 5,679,659 A | 10/1997 | Verhoeven et al. | 514/56 |
| 5,684,061 A | 11/1997 | Ohnishi et al. | 523/114 |
| 5,691,311 A | 11/1997 | Maraganore et al. | 514/12 |
| 5,693,085 A | 12/1997 | Buirge et al. | 623/1.13 |
| 5,697,967 A | 12/1997 | Dinh et al. | 128/898 |
| 5,697,971 A | 12/1997 | Fischell et al. | 623/1.15 |
| 5,700,286 A | 12/1997 | Tartaglia et al. | 623/1.15 |
| 5,707,385 A | 1/1998 | Williams | 606/192 |
| 5,709,874 A | 1/1998 | Hanson et al. | 424/423 |
| 5,713,949 A | 2/1998 | Jayaraman | 623/1.12 |
| 5,716,981 A | 2/1998 | Hunter et al. | 514/449 |
| 5,725,549 A | 3/1998 | Lam | 623/1.15 |
| 5,725,567 A | 3/1998 | Wolff et al. | 623/1.42 |
| 5,728,150 A | 3/1998 | McDonald et al. | 623/1.15 |
| 5,728,420 A | 3/1998 | Keogh | 427/2.12 |
| 5,731,326 A | 3/1998 | Hart et al. | 514/323 |
| 5,733,327 A | 3/1998 | Igaki et al. | 623/1.5 |
| 5,733,920 A | 3/1998 | Mansuri et al. | 514/337 |
| 5,733,925 A | 3/1998 | Kunz et al. | 514/449 |
| 5,735,897 A | 4/1998 | Buirge | 623/1.15 |
| 5,739,138 A | 4/1998 | Bianco et al. | 514/263.36 |
| 5,755,734 A | 5/1998 | Richter et al. | 606/194 |
| 5,755,772 A | 5/1998 | Evans et al. | 128/898 |
| 5,759,205 A | 6/1998 | Valentini | 433/173 |
| 5,769,883 A | 6/1998 | Buscemi et al. | 623/1.42 |
| 5,776,184 A | 7/1998 | Tuch | 623/1.11 |
| 5,780,476 A | 7/1998 | Underiner et al. | 514/263.36 |
| 5,782,908 A | 7/1998 | Cahalan et al. | 623/1.13 |
| 5,788,979 A | 8/1998 | Alt et al. | 424/426 |
| 5,792,106 A | 8/1998 | Mische | 604/103.01 |
| 5,792,772 A | 8/1998 | Bianco et al. | 514/263.36 |
| 5,798,372 A | 8/1998 | Davies et al. | 514/356 |
| 5,799,384 A | 9/1998 | Schwartz et al. | 29/458 |
| 5,800,507 A | 9/1998 | Schwartz | 623/1.11 |
| 5,800,508 A | 9/1998 | Goicoechea et al. | 623/1.15 |
| 5,807,861 A | 9/1998 | Klein et al. | 514/263.35 |
| 5,811,447 A | 9/1998 | Kunz et al. | 514/411 |
| 5,820,917 A | 10/1998 | Tuch | 427/2.1 |

| | | | | | | | |
|---|---|---|---|---|---|---|---|
| 5,820,918 A | 10/1998 | Ronan et al. | 427/2.1 | 6,273,913 B1 | 8/2001 | Wright et al. | 623/1.42 |
| 5,824,048 A | 10/1998 | Tuch | 128/898 | 6,284,305 B1 | 9/2001 | Ding et al. | 427/2.28 |
| 5,824,049 A | 10/1998 | Ragheb et al. | 623/1.44 | 6,287,320 B1 | 9/2001 | Slepian | 606/194 |
| 5,827,587 A | 10/1998 | Fukushi | 428/36.6 | 6,287,628 B1 | 9/2001 | Hossainy et al. | 427/2.3 |
| 5,833,651 A | 11/1998 | Donovan et al. | 604/509 | 6,299,604 B1 | 10/2001 | Ragheb et al. | 604/265 |
| 5,837,008 A | 11/1998 | Berg et al. | 128/898 | 6,306,144 B1 | 10/2001 | Sydney et al. | 606/108 |
| 5,837,313 A | 11/1998 | Ding et al. | 427/2.21 | 6,306,166 B1 | 10/2001 | Barry et al. | 623/1.46 |
| 5,843,120 A | 12/1998 | Israel et al. | 623/1.15 | 6,306,176 B1 | 10/2001 | Whitbourne | 623/23.59 |
| 5,843,166 A | 12/1998 | Lentz et al. | 623/1.13 | 6,306,421 B1 | 10/2001 | Kunz et al. | 424/423 |
| 5,843,172 A | 12/1998 | Yan | 623/1.42 | 6,309,380 B1 | 10/2001 | Larson et al. | 604/502 |
| 5,849,034 A | 12/1998 | Schwartz | 606/36 | 6,309,660 B1 | 10/2001 | Hsu et al. | 424/425 |
| 5,851,217 A | 12/1998 | Wolff et al. | 606/191 | 6,313,264 B1 | 11/2001 | Caggiano et al. | 530/350 |
| 5,851,231 A | 12/1998 | Wolff et al. | 623/1.42 | 6,316,018 B1 | 11/2001 | Ding et al. | 424/423 |
| 5,858,990 A | 1/1999 | Walsh | 514/44 | 6,335,029 B1 | 1/2002 | Kamath et al. | 424/423 |
| 5,861,027 A | 1/1999 | Trapp | 623/1.15 | 6,358,556 B1 | 3/2002 | Ding et al. | 427/2.24 |
| 5,865,814 A | 2/1999 | Tuch | 623/1.15 | 6,369,039 B1 | 4/2002 | Palasis et al. | 424/93.2 |
| 5,871,535 A | 2/1999 | Wolff et al. | 128/898 | 6,379,382 B1 | 4/2002 | Yang | 623/1.42 |
| 5,873,904 A | 2/1999 | Ragheb et al. | 623/1.13 | 6,387,121 B1 | 5/2002 | Alt | 623/1.15 |
| 5,876,433 A | 3/1999 | Lunn | 623/1.15 | 6,403,635 B1 | 6/2002 | Kinsella et al. | 514/449 |
| 5,877,224 A | 3/1999 | Brocchini et al. | 514/772.2 | 6,407,067 B1 | 6/2002 | Schafer | 514/19 |
| 5,879,697 A | 3/1999 | Ding et al. | 424/422 | 6,517,858 B1 | 2/2003 | Le Moel et al. | 424/424 |
| 5,882,335 A | 3/1999 | Leone et al. | 604/103.02 | 6,517,889 B1 | 2/2003 | Jayaraman | 427/2.24 |
| 5,891,108 A | 4/1999 | Leone et al. | 604/264 | 6,545,097 B2 | 4/2003 | Pinchuk et al. | 525/240 |
| 5,893,840 A | 4/1999 | Hull et al. | 604/103.02 | 6,585,764 B2 | 7/2003 | Wright et al. | 623/1.42 |
| 5,897,911 A | 4/1999 | Loeffler | 427/2.25 | 6,620,194 B2 | 9/2003 | Ding et al. | 623/1.43 |
| 5,900,246 A | 5/1999 | Lambert | 424/429 | 6,746,773 B2 | 6/2004 | Llanos et al. | 428/421 |
| 5,902,266 A | 5/1999 | Leone et al. | 604/509 | 6,776,796 B2 | 8/2004 | Falotico et al. | 623/1.46 |
| 5,916,910 A | 6/1999 | Lai | 514/423 | 6,808,536 B2 | 10/2004 | Wright et al. | 623/1.42 |
| 5,922,393 A | 7/1999 | Jayaraman | 427/2.3 | 2001/0007083 A1 | 7/2001 | Roorda | 623/1.15 |
| 5,932,243 A | 8/1999 | Fricker et al. | 424/450 | 2001/0029351 A1 | 10/2001 | Falotico et al. | 604/103.02 |
| 5,932,299 A | 8/1999 | Katoot | 427/508 | 2001/0029660 A1 | 10/2001 | Johnson | 29/557 |
| 5,932,580 A | 8/1999 | Levitzki et al. | 181/152 | 2001/0032014 A1 | 10/2001 | Yang et al. | 623/1.15 |
| 5,951,586 A | 9/1999 | Berg et al. | 606/198 | 2001/0034363 A1 | 10/2001 | Li et al. | 514/449 |
| 5,957,971 A | 9/1999 | Schwartz | 623/1.15 | 2001/0037145 A1 | 11/2001 | Guruwaiya et al. | 623/1.15 |
| 5,968,091 A | 10/1999 | Pinchuk et al. | 623/1.16 | 2002/0010418 A1 | 1/2002 | Lary et al. | 604/101.04 |
| 5,972,027 A | 10/1999 | Johnson | 623/1.42 | 2002/0032477 A1 | 3/2002 | Helmus et al. | 623/1.2 |
| 5,976,534 A | 11/1999 | Hart et al. | 424/145.1 | 2002/0041899 A1 | 4/2002 | Chudzik et al. | 424/487 |
| 5,977,163 A | 11/1999 | Li et al. | 514/449 | 2002/0061326 A1 | 5/2002 | Li et al. | 424/424 |
| 5,980,553 A | 11/1999 | Gray et al. | 623/1.15 | 2002/0068969 A1 | 6/2002 | Shanley et al. | 623/1.16 |
| 5,980,566 A | 11/1999 | Alt et al. | 623/23.7 | 2002/0071902 A1 | 6/2002 | Ding et al. | 427/2.24 |
| 5,980,972 A | 11/1999 | Ding | 427/2.24 | 2002/0082680 A1 | 6/2002 | Shanley et al. | 623/1.16 |
| 5,981,568 A | 11/1999 | Kunz et al. | 514/411 | 2002/0082685 A1 | 6/2002 | Sirhan et al. | 623/1.42 |
| 5,985,307 A | 11/1999 | Hanson et al. | 424/423 | 2002/0091433 A1 | 7/2002 | Ding et al. | 623/1.2 |
| 5,997,468 A | 12/1999 | Wolff et al. | 606/36 | 2002/0095114 A1 | 7/2002 | Palasis | 604/96.01 |
| 6,004,346 A | 12/1999 | Wolff et al. | 623/23.71 | 2002/0099438 A1 | 7/2002 | Furst | 623/1.16 |
| 6,015,432 A | 1/2000 | Rakos et al. | 623/1.13 | 2002/0103526 A1 | 8/2002 | Steinke | 623/1.11 |
| 6,039,721 A | 3/2000 | Johnson et al. | 604/508 | 2002/0119178 A1 | 8/2002 | Levesque et al. | 424/423 |
| 6,059,813 A | 5/2000 | Vrba et al. | 606/198 | 2002/0123505 A1 | 9/2002 | Mollison et al. | 514/291 |
| 6,071,305 A | 6/2000 | Brown et al. | 623/1.43 | 2002/0127327 A1 | 9/2002 | Schwartz et al. | 427/2.15 |
| 6,074,659 A | 6/2000 | Kunz et al. | 424/423 | 2002/0133222 A1 | 9/2002 | Das | 623/1.16 |
| 6,080,190 A | 6/2000 | Schwartz | 623/1.22 | 2002/0133224 A1 | 9/2002 | Bajgar et al. | 623/1.39 |
| 6,096,070 A | 8/2000 | Ragheb et al. | 623/1.39 | 2002/0165608 A1 | 11/2002 | Llanos | 604/500 |
| 6,120,536 A | 9/2000 | Ding et al. | 623/1.43 | 2002/0193475 A1 | 12/2002 | Hossainy et al. | 524/113 |
| 6,120,847 A | 9/2000 | Yang et al. | 427/335 | 2003/0065377 A1 | 4/2003 | Davila et al. | 604/265 |
| 6,136,798 A | 10/2000 | Cody et al. | 514/141 | 2003/0216699 A1 | 11/2003 | Falotico | 604/265 |
| 6,140,127 A | 10/2000 | Sprague | 435/395 | 2004/0049265 A1 | 3/2004 | Ding et al. | 623/1.42 |
| 6,146,358 A | 11/2000 | Rowe | 604/103 | 2004/0243097 A1 | 12/2004 | Falotico et al. | 604/500 |
| 6,153,252 A | 11/2000 | Hossainy et al. | 427/2.3 | 2004/0260268 A1 | 12/2004 | Falotico et al. | 604/500 |
| 6,159,488 A | 12/2000 | Nagier et al. | 424/423 | 2005/0002986 A1 | 1/2005 | Falotico et al. | 424/426 |
| 6,171,232 B1 | 1/2001 | Papandreou et al. | 600/36 | 2005/0004663 A1 | 1/2005 | Llanos et al. | 623/1.46 |
| 6,171,609 B1 | 1/2001 | Kunz | 424/422 | 2005/0033261 A1 | 2/2005 | Falotico et al. | 604/500 |
| 6,177,272 B1 | 1/2001 | Nabel et al. | 435/320.1 | 2005/0106210 A1 | 5/2005 | Ding et al. | 424/423 |
| 6,179,817 B1 | 1/2001 | Zhong | 604/265 | 2005/0187611 A1 | 8/2005 | Ding et al. | 623/1.15 |
| 6,193,746 B1 | 2/2001 | Strecker | 623/1.13 | 2005/0208200 A1 | 9/2005 | Ding et al. | 427/2.25 |
| 6,214,901 B1 | 4/2001 | Chudzik et al. | 623/113 | 2006/0088654 A1 | 4/2006 | Ding et al. | 427/2.21 |
| 6,225,346 B1 | 5/2001 | Tang et al. | 514/623 | 2006/0089705 A1 | 4/2006 | Ding et al. | 623/1.15 |
| 6,240,616 B1 | 6/2001 | Yan | 29/527.2 | | | | |
| 6,245,537 B1 | 6/2001 | Williams et al. | 435/135 | | | FOREIGN PATENT DOCUMENTS | |
| 6,251,920 B1 | 6/2001 | Grainger et al. | 514/319 | | | | |
| 6,254,632 B1 | 7/2001 | Wu et al. | 623/1.15 | DE | 19723723 A1 | 12/1998 | |
| 6,254,634 B1 | 7/2001 | Anderson et al. | 623/1.42 | EP | 0 145 166 A2 | 6/1985 | |
| 6,258,121 B1 | 7/2001 | Yang et al. | 623/1.46 | EP | 0 177 330 A2 | 4/1986 | |
| 6,268,390 B1 | 7/2001 | Kunz | 514/411 | EP | 0 183 372 A1 | 6/1986 | |

| | | |
|---|---|---|
| EP | 0 221 570 A2 | 5/1987 |
| EP | 0 421 729 A2 | 4/1991 |
| EP | 0 540 290 A2 | 5/1993 |
| EP | 0 568 310 A1 | 11/1993 |
| EP | 0 604 022 A1 | 6/1994 |
| EP | 0 621 015 A1 | 10/1994 |
| EP | 0 623 354 A1 | 11/1994 |
| EP | 0 712 615 A1 | 5/1996 |
| EP | 0 716 836 A1 | 6/1996 |
| EP | 0 734 721 A2 | 10/1996 |
| EP | 0 747 069 A2 | 12/1996 |
| EP | 0 761 251 A1 | 3/1997 |
| EP | 0 800 801 A1 | 10/1997 |
| EP | 0 540 290 B1 | 1/1998 |
| EP | 0 830 853 A1 | 3/1998 |
| EP | 0 815 803 A1 | 7/1998 |
| EP | 0 850 651 A2 | 7/1998 |
| EP | 0 938 878 A2 | 9/1999 |
| EP | 0 938 878 A3 | 9/1999 |
| EP | 0 950 386 A2 | 10/1999 |
| EP | 0 968 688 A1 | 1/2000 |
| EP | 0 633 032 B1 | 2/2001 |
| EP | 1 192 957 A2 | 4/2002 |
| EP | 1 588 726 A1 | 10/2005 |
| EP | 1 588 727 A1 | 10/2005 |
| FR | 566 807 A1 | 4/1992 |
| GB | 0 662 307 A2 | 12/1951 |
| GB | 1 205 743 A | 9/1970 |
| GB | 2 135 585 A | 9/1984 |
| JP | 0 734 698 A2 | 3/1996 |
| SU | 660689 | 5/1979 |
| SU | 1457921 | 2/1989 |
| WO | 89/03232 A1 | 4/1989 |
| WO | 91/12779 A1 | 9/1991 |
| WO | 92/15286 A1 | 9/1992 |
| WO | 94/01056 A1 | 1/1994 |
| WO | 94/21308 A1 | 9/1994 |
| WO | 94/21309 A1 | 9/1994 |
| WO | 94/24961 A1 | 11/1994 |
| WO | 96/00272 A1 | 1/1996 |
| WO | 96/26689 A1 | 9/1996 |
| WO | 96/32907 A1 | 10/1996 |
| WO | 96/34580 A1 | 11/1996 |
| WO | 97/25000 A1 | 7/1997 |
| WO | 97/33534 A1 | 9/1997 |
| WO | 98/08463 A1 | 3/1998 |
| WO | 98/13344 A1 | 4/1998 |
| WO | 98/19628 A1 | 5/1998 |
| WO | 98/23228 A1 | 6/1998 |
| WO | 98/23244 A1 | 6/1998 |
| WO | 98/34669 A1 | 8/1998 |
| WO | 98/36784 A1 | 8/1998 |
| WO | 98/47447 A1 | 10/1998 |
| WO | 98/56312 A1 | 12/1998 |
| WO | 00/21584 A1 | 4/2000 |
| WO | 00/27445 A1 | 5/2000 |
| WO | 00/27455 A1 | 5/2000 |
| WO | 00/32255 A1 | 6/2000 |
| WO | 00/38754 A1 | 7/2000 |
| WO | 01/87342 A2 | 11/2001 |
| WO | 01/87372 A1 | 11/2001 |
| WO | 01/87373 A1 | 11/2001 |
| WO | 01/87376 A1 | 11/2001 |
| WO | 02/26139 A1 | 4/2002 |
| WO | 02/26271 A1 | 4/2002 |
| WO | 02/26280 A1 | 4/2002 |
| WO | 02/26281 A1 | 4/2002 |
| WO | 03/015664 A1 | 2/2003 |
| WO | 03/057218 A1 | 7/2003 |

OTHER PUBLICATIONS

U.S. Appl. No. 08/424,884, filed Apr. 19, 1995, Helmus et al.
U.S. Appl. No. 08/526,273, filed Sep. 11, 1995, Ding.
U.S. Appl. No. 08/730,542, filed Oct. 11, 1996, Helmus.
U.S. Appl. No. 09/575,480, filed May 19, 2000, Kopia.
U.S. Appl. No. 10/431,059, filed May 7, 2003, Falotico.
U.S. Appl. No. 10/829,074, filed Apr. 21, 2004, Falotico et al.
U.S. Appl. No. 10/833,200, filed Apr. 27, 2004, Falotico et al.
U.S. Appl. No. 10/852,517, filed May 24, 2004, Falotico et al.
Abraham, R. T., "Mammalian target of rapamycin: Immunosupressive drugs offer new insight into cell growth regualtion," *Progress in Inflammation Research*, 2000, Switzerland.
Alvarado, R. et al., "Evaluation of Polymer-coated Balloon-expandable Stents in Bile Ducts," *Radiology*, 1989, 170, 975-978.
Badimon, J. J. et al., "Inhibitory Effects of Rapamycin on Intimal Hyperplasia After PTCA," *JACC*, Mar. 1998.
Bailey et al., "Polymer Coating of Palmaz-Schatz Stent Attenuates Vascular Spasm after Stent Placement," *Circulation*, 82:III-541 (1990).
Berk, B. C. et al., "Pharmacologic Roles of Heparin and Glucocorticoids to Prevent Restenosis After Coronary Angioplasty," *JACC*, May 1991, 17(6), 111B-117B.
Bertram, P. G. et al., "The 14-3-3 proteins positively regulate rapamycin-sensitive signaling," *Current Biology*, 1998, 8, 1259-1267.
Biomaterials Science (B.D. Ratner, Ed.), Academic Press, New York, NY, pp. 228-238, 1996.
Campbell, G. R. et al., "Phenotypic Modulation of Smooth Muscle Cells in Primary Culture, Vascular Smooth Muscle Cells in Culture," *CRC Press*, 1987, 39-55.
Chang, M. W. et al., "Adenovirus-mediated Over-expression of the Cyclin/Cyclin-dependent Kinase inhibitor, p. 21 inhibits Vascular Smooth Muscle Cell Proliferation and Neointima Formation in the Rat Carotid Artery Model of Balloon Angioplasty," *J. Clin. Invest.*, 1995, 96, 2260-2268.
Chung, J. et al., "Rapamycin-FKBP specifically blocks growth-dependent activation of and signaling by the 70 kd S6 protein kinases," *Cell*, Jun. 26, 1992, 69(7), 1227-1236.
Clowes, A. W. et al., "Kinetics of cellular proliferation after arterial injury. IV. Heparin inhibits rat smooth muscle mitogenesis and migration," *Circ. Res.*, 1986, 58(6), 839-845.
Clowes, A. W. et al., Kinetics of Cellular Proliferation after Arterial Injury, *Laboratory Investigation*, 1985, 52(6), 611-616.
Clowes, A. W. et al., "Significance of quiescent smooth muscle migration in the injured rat carotid artery," *Circ Res.* 1985, 56(1), 139-145.
Clowes, A. W., "Suppression by heparin of smooth muscle cell proliferation in injured arteries," *Nature*, 1977, 265(5595), 625-626.
Colburn, M. D. et al., "Dose responsive suppression of myointimal hyperplasia by dexamethasone," *J.Vasc. Surg.*, 1992, 15, 510-518.
Currier, J. W. et al., "Colchicine Inhibits Restenosis After Iliac Angioplasty in the Atherosclerotic Rabbit," *Circ.*, 1989, 80(4), 11-66 (Abstract No. 0263).
Encyclopedia of Polymer Science and Engineering, vol. 7, Fluorcarbon Elastomers, p. 257-267, Mar. 1989.
Farb, A. et al., "Vascular smooth muscle cell cytotoxicity and sustained inhibition of neointimal formation by fibroblast growth factor 2-saporin fusion protein," *Circ. Res.*, 1997, 80, 542-550.
Ferns, G. A. A. et al., "Inhibition of Neointimal Smooth Muscle Accumulation After Angioplasty by an Antibody to PDGF," *Science*, 1991, 253, 1129-1132.
Fischman, D. L. et al., "A Randomized Comparison of Coronary-Stent Placement and Balloon Angioplasty in the Treatment of Coronary Artery Disease," *N. Eng. J. Med.*, Aug. 25, 1994, 331(8), 496-501.
Franklin, S. M. et al., "Pharmacologic prevention of restenosis after coronary angioplasty: review of the randomized clinical trials," *Coronary Artery Disease* Mar. 1993, 4(3), 232-242.

Fukuyama, J. et al., "Tranilast suppresses the vascular intimal hyperplasia after balloon injury in rabbits fed on a high-cholesterol diet," *Eur. J. Pharmacol.*, 1996, 318, 327-332.

Gregory, C. R. et al., "Rapamycin Inhibits Arterial Intimal Thickening Caused by Both Alloimmune and Mechanical Injury," *Transplantation*, Jun. 1993, 55(6), 1409-1418.

Gregory, C. R. et al, "Treatment with Rapamycin and Mycophenolic Acid Reduces Arterial Intimal Thickening Produced by Mechanical Injury and Allows Endothelial Replacement," *Transplantation*, Mar. 15, 1995, 59(5), 655-661.

Guyton, J. R. et al., "Inhibition of rat arterial smooth muscle cell proliferation by heparin. In vivo studies with anticoagulant and nonanticoagulant heparin," *Circ. Res.*, 1980, 46, 625-634.

Hansson, G. K. et al., "Interferon-γ Inhibits Arterial Stenosis After Injury," *Circ.*, 1991, 84, 1266-1272.

Hashemolhosseini, S. et al., "Rapamycin Inhibition of the G1 to S Transition Is Mediated by Effects on Cyclin D1 mRNA and Protein Stability," *J Biol Chem*, Jun. 5, 1998, 273, 14424-14429.

Jonasson, J. et al., "Cyclosporin A inhibits smooth muscle proliferation in the vascular response to injury," *Proc. Natl., Acad. Sci.*, 1988, 85, 2303-2306.

Kuhnt, M. et al., "Microbial Conversion of Rapamycin," *Enzyme and Microbial Technology*, 1997, 21, 405-412.

Lange, R. A. MD et al., "Restenosis After Coronary Balloon Angioplasty," *Annu. Rev. Med.*, 1991, 42, 127-132.

Liu, M. W. et al., "Trapidil in Preventing Restenosis After Balloon Angioplasty in the Atherosclerotic Rabbit," *Circ.*, 1990, 81, 1089-1093.

Liu, M. W., MD et al., "Restenosis After Coronary Angioplasty Potential Biologic Determinants and Role of Intimal Hyperplasia," *Circulation*, 1989, 79, 1374-1387.

Lundergan, C. F. et al., "Peptide inhibition of Myointimal Proliferation by Angiopeptin, a Somatostatin Analogue," *JACC*, May 1991, 17(6), 132B-136B.

Majesky, M. W. et al., "Heparin regulates smooth muscle S phase entry in the injured rat carotoid artery," *Circ. Res.*, 1987, 61, 296-300.

Marx, S. O. et al., "Rapamycin-FKBP Inhibits Cell Cycle Regulators of Proliferation in Vascular Smooth Muscle Cells," *Circ. Res.*, 1995, 76, 412-417.

Nemecek, G. M. et al., "Terbinafine Inhibits the Mitogenic Response to Platelet—Derived Growth Factor in Vitro and Neoinimal Proliferation in Vivo," *J. Pharmacol. Exp. Thera.*, 1989, 248, 1167-1174.

Okada, T. et al., "Localized Release of Perivascular Heparin Inhibits Intimal Proliferation after Endothelial Injury without Systemic Anticoagulation," *Neurosurgery*, 1989, 25, 892-898.

Poon, M. et al., "Rapamycin Inhibits Vascular Smooth Muscle Cell Migration," *J. Clin Invest.*, Nov. 1996, 98(10), 2277-2283.

Popma, J. J. et al., "Clinical trials of restenosis after coronary angioplasty," *Circulation*, Sep. 1991, 84(3), 1426-1436.

Powell, J. S. et al., "Inhibitors of Angiotensin-Converting Enzyme Prevent Myointimal Proliferation After Vascular Injury," *Science*, 1989, 245, 186-188.

Rensing, B. J. et al., Coronary restenosis elimination with a sirolimus eluting stent, *European Heart Journal*, 2001, 22, 2125-2130.

Rodeck, C. et al., "Methods for the Transcervical Collection of Fetal Cells During the First Trimester of Pregnancy," *Prenatal Diagnosis*, 1995, 15, 933-942.

Ruef, J. MD, et al., "Flavopiridol Inhibits Muscle Cell Proliferation In Vitro and Neointimal Formation In Vitro After Carotid Injury in the Rat," From the Division of Cardiology and Sealy Center for Molecular Cardiology, University of Texas Medical Branch, Galveston; Accepted Apr. 9, 1999; *Circulation* Aug. 10, 1999, pp. 659-665.

Serruys, P. W. et al., "A comparison of balloon-expandable-stent implantation with balloon angioplasty in patients with coronary artery disease," *N Engl J Med*, Aug. 25, 1994; 331(8), 489-495.

Serruys, P. W. et al., "Evaluation of ketanserin in the prevention of restenosis after percutaneous transluminal coronary angioplasty. A multicenter randomized double-blind placebo-controlled trial," *Circulation*. Oct. 1993; 88(4 Pt 1), 1588-1601.

Serruys, P. W. et al., "Heparin-coated Palmaz-Schatz stents in human coronary arteries. Early outcome of the Benestent-II Pilot Study," *Circulation*, Feb. 1, 1996; 93(3), 412-422.

Siekierka, J. J., "Probing T-Cell Signal Transduction Pathways with the Immunosupressive Drugs, FK-506 and Rapamycin," *Immunologic Research*, 1994, 13, 110-116.

Sigwart, et al., "Intravascular Stents to Prevent Occlusion and Restenosis After Transluminal Angioplasty," *N. Engl. J. Med.*, Mar. 19, 1987, 316, 701-706.

Simons, M. et al., "Antisense c-*myb* oligonucleotides inhibit intimal arterial smooth muscel cell accumulation in vivo," *Nature*, 1992, 359, 67-70.

Snow, A. D. et al., "Heparin modulates the composition of the extracellular matrix domain surrounding arterial smooth muscle cells," *Am. J. Pathol.*, 1990, 137, 313-330.

Sollott, S. J. et al., "Taxol Inhibits Neoitimal Smooth Muscle Cell Accumulation after Angioplasty in the Rat," *J. Clin. Invest.*, 1995, 95, 1869-1876.

van Det Giessen, et al., "Self-expandable Mesh Stents: an Experimental Study Comparing Polymer Coated and Uncoated Wallstent Stents in the Coronary Circulation of Pigs," *Circulation* 1990, 82(suppl. III):III-542 van Der Giessen, W. J. et al., "Coronary stenting with polymer-coated and uncoated self-expanding endoprostheses in pigs," Coron. Art. Disease 1992; 3, 631-640.

Vasey, C. G. et al., "Clinical Cardiology: Stress Echo and Coronary Flow", , *Circulation*, Oct. 1989, 80(4) Supplement II, II-66.

Verweire, E. et al., "Evaluation of Fluorinated Polymers As Coronary Stent Coating," *Journal of Materials Science: Materials in Medicine*, Apr. 2000.

Weinberger, J. et al., "Intracoronary irradiation: dose response for the prevention of restenosis in swine," *Int. J. Rad. Onc. Biol. Phys.*, 1996, 36, 767-775.

Preliminary Amendment in U.S. Appl. No. 07/258,189, May 22, 1989.

Trial Transcript from Nov. 6, 2000 at 185-90 and 235-36 (Attorneys' opening remarks regarding '984 patent).

Trial Transcript from Nov. 7, 2000 at 274-301, 307-315, 320-28 and 332 (Cordis expert testimony regarding the Palmaz-Schatz stent); 370-379, 480-496 (J. Palmaz testimony regarding the Palmaz-Schatz stent, the '984 patent and the connected z-stent art).

Trial Transcript from Nov. 8, 2000 at 547-63, 657-63, 674-722, 782-85 (Cordis expert testimony regarding the Palmaz-Schatz stent, the '984 patent and the connected z-stent art).

Trial Transcript from Nov. 9, 2000 at 819-23, 921 (Cordis expert testimony regarding the '984 patent); 926-941 . (R. Croce testimony re Palmaz-Schatz stent); 1033-1053. (R. Schatz testimony).

Trial Transcript from Nov. 13, 2000 at 1089-1 134. (R. Schatz testimony); 1275-1305 (Cordis expert testimony regarding the '984 patent).

Trial Transcript from Nov. 14, 2000 at 1390-1404, 1448-1454, 1486-1500 (Cordis expert testimony regarding the '984 patent).

Trial Transcript from Nov. 15, 2000 at 1686-87, 1724-42, 1828-34, 1850-54, 1887-92 (AVE expert testimony regarding the '984 patent).

Trial Transcript from Nov. 16, 2000 at 2077-198 (AVE expert testimony regarding the alleged obviousness of the '984 patent).

Trial Transcript from Nov. 17, 2000 at 2331-34 ( jury instructions as to the meaning of the limitations of the claims of the '984 patent).

Trial Transcript from Nov. 20, 2000 at 2441-48, 2499-2500, 2546-50, 2552-56 (Attorneys' closing arguments regarding the '984 patent).

Trial Transcript from Nov. 21, 2000 at 2592-94 (reading of jury verdict).

Trial Transcript from Dec. 18, 2000 at 2750-95 (Cordis expert testimony regarding the Palmaz-Schatz stent during the damages phase).

Trial Transcript from Dec. 20, 2000 at 3421-88 (AVE expert testimony regarding the Palmaz-Schatz stent during the damages phase).

Jury verdict, dated Nov. 21, 2000.

District Court decisions on post-trial motions (194 F. Supp. 2d 323).

Court of Appeal for the Federal Circuit decision (339 F.3d 1352).

Trial Transcript from Mar. 4, 2005 at 133-135, 171-173 and 192-96 (Attorney's opening remarks regarding '984 validity).
Trial Transcript from Mar. 7, 2005 at 275-31 1 (Cordis expert testimony regarding the Palmaz-Schatz stent); 342-46, 353-59, 416-425 (J. Palmaz testimony regarding the Palmaz-Schatz stent, the '984 patent and the connected z-stent art); 430-449, 452-58, 462-492 (R. Croce testimony regarding the Palmaz-Schatz stent); 500-507 (Cordis expert testimony regarding the '984 patent).
Trial Transcript from Mar. 8, 2005 at 609 (Cordis expert testimony regarding the '984 patent); 628-73, 724-740, 773, 801-839 (Cordis expert testimony regarding the '984 patent, the prior art and the Palmaz-Schatz stent).
Trial Transcript from Mar. 9, 2005 at 936-49, 968-69 (Cordis expert testimony regarding the '984 patent, the prior art and the Palmaz-Schatz stent).
Trial Transcript from Mar. 10, 2005 at 1427-74, 178-1509, 1514-23 (AVE expert testimony regarding the alleged obviousness of the '984 patent); 1566-93 (AVE expert testimony regarding Palmaz-Schatz stent); 1634-49 (R. Schatz testimony).
Trial Transcript from Mar. 11, 2005 at 1846-47, 1891-1900, 1919 (Attorneys' closing arguments regarding '984 obviousness).
Trial Transcript from Mar. 14, 2005 at 1964-67 (reading of jury verdict).
Jury verdict dated Mar. 14, 2005.
Medtronic Vascular Inc.'s Opening Brief in Support of Its Motion for Judgment As a Infringement Claim dated Apr. 19, 2005.
Medtronic Vascular Inc.'s Opening Brief in Support of Its Motion for a New Trial dated Apr. 19, 2005.
D.I. 1407, Cordis' Combined Answering Brief In Opposition to AVE's Motion for JMOL on Infringement of the Palmaz '762 and Schatz '984 Patents and Its Motion for a New Trial dated May 5, 2005.
D.I. 1414, Medtronic Vascular Inc.'s Combined Reply Brief In Support of Its Motion for Judgment as a Matter of Law on Cordis Corp.'s Patent Infringement Claims and Its Motion for a New Trial dated May 19, 2005.
Trial Transcript from Feb. 8, 2001 at 372-412, 449-469 (B. Tobor testimony regarding the prosecution of the '417, '984 and '332 patents); 510-13 (J. Milnamow testimony regarding the prosecution of the '332 patent); 558-604 (J. Palmaz testimony regarding the prosecution of the '417, '984 and '332 patents and the prior art).
Trial Transcript from Feb. 9, 2001 at 637-45, 662-672, 682-85 (J. Palmaz testimony regarding the prior art); 699-742 (R. Schatz testimony); 769-770, 790-95 (Cordis expert testimony regarding prior art).
D.I. 1067, Medtronic AVE, Inc.'s Post-Trial Brief Relating to the Unenforceability of the '762 and '984 Patents Due to Inequitable Conduct.
D.I. 1077, Cordis' Combined Answering Brief in Opposition to AVE's BSC's Post-Hearing Briefs on Alleged Inequitable Conduct Concerning the '762, '984 and '332 Patents.
D.I. 1089, Reply Brief In Support of Medtronic AVE, Inc.'s Contention that the '762 and '984 Patents are Unenforceable Due to Inequitable Conduct dated May 7, 2001.
C.A. No. 00-886-SLR, Answer and Counterclaims of Def. Medtronic AVE, Inc. To First Amended Complaint of Plaintiff Cordis Corp.
BSC's Opening Post-Trial Brief in Support of Its Defense That the Patents in Suit Are Unenforceable, dated Mar. 16, 2001.
Reply Brief in Support of BSC's Defense That the Patents in Suit Are Unenforceable, dated May 7, 2001.
Court's Decision on allegations of inequitable conduct (194 F. Supp. 2d 323) Mar. 28, 2002.
Trial Transcript from Nov. 21, 2000 at 155-57 and 180-84 (Attorneys' opening remarks regarding '332 patent).
Trial Transcript from Nov. 27, 2000 at 227-51, 260-300 (Cordis expert testimony regarding the Palmaz-Schatz stent); 343-60, 363-67, 424-33 (J. Palmaz testimony regarding the Palmaz-Schatz stent and the '332 patent).
Trial Transcript from Nov. 28, 2000 at 649-71.
Trial Transcript from Nov. 29, 2000 at 791-816, 859-870, 953-62 (Cordis expert testimony regarding the '332 patent and the Palmaz-Schatz stent).

Trial Transcript from Nov. 30, 2000 at 1018 (Cordis expert testimony regarding the '332 patent); 1062-80, 1 108-1 1 1 1 (R. Croce testimony regarding the Palmaz-Schatz stent); 1 169-70, 1205-17, 1236-45 (Cordis expert testimony regarding the '332 patent).
Trial Transcript from Dec. 1, 2000 at 1352-54 (Cordis expert testimony regarding the '332 patent); 1364-1442 (R. Schatz testimony); 1493-1508, 1552-69 (BSC expert testimony regarding the '332 patent and the Palmaz-Schatz stent).
Trial Transcript from Dec. 4, 2000 at 1602-12, 1638-51, 1713-14, 1730-61, 1811-14, 1823-36 (BSC expert testimony regarding the alleged obviousness of the '332 patent, the prior art and the Palmaz-Schatz stent).
Trial Transcript from Dec. 6, 2000 at 2318-27, 2342-58 (BSC expert testimony regarding the '332 patent).
Trial Transcript from Dec. 7, 2000 at 2549-52 (Cordis expert testimony regarding the '332 patent); 2575-2579, 2591-92, 2630-31, 2649, 2669-71, 2684-85, 2688, 2708-10, 2725-27 (Attorney closing argument regarding '332 patent); 2742-46 Q'ury instructions as to the meaning of the limitations of the claims of the '332 patent).
Trial Transcript from Dec. 11, 2000 at 2817-22 (reading of jury verdict).
Jury verdict, dated Dec. 11, 2000.
D.I. 699, Motion by Defendant BSC and Scimed Life Systems, Inc. For Summary Judgment of Invalidity of U.S. Patent No. 5,902,332 dated Apr. 4, 2000.
D.I.896, Order Denying Motion for Summary Judgment of Invalidity and Unenforceability of Claims 1, 3, and 5 of the U.S. Patent No. 5,902,332 Denying {699-1} Motion for Summary Judgment of Invalidity of U.S. Patent No. 5,902,332 dated Oct. 12, 2000.
Wright et al., Percutaneous Endovascular Stent: An Experimental Study (Abstract), RSNA Meeting (Nov. 28, 1984).
Hearing Transcript from Feb. 10, 1998 at 122-32, 146-80 (Attorneys' opening remarks regarding '417 patent); 180-312 (R. Schatz testimony) [Portions of This Transcript Have Been Removed as Confidential].
Hearing Transcript from Feb. 11, 1998 at 427-575, 577-651 (Cordis expert testimony regarding the '417 patent, the prior art and the Palmaz-Schatz stent).
Hearing Transcript from Feb. 13, 1998 at 1121-1261 (Guidant expert testimony regarding the alleged obviousness of the '417 patent, the prior art and the Palmaz-Schatz stent). [Portions of This Transcript Have Been Removed as Confidential].
Order by J. Robinson denying Cordis' Motion for a Preliminary Injunction Against ACS dated Jul. 17, 1998.
ACS, Inc. 's and Guidant Corp.'s Opening Brief in Support of Their Motion for Summary Judgment on Invalidity of U.S. Patent No. 5,102,417 dated Aug. 27, 1998.
Plaintiffs ' Answering Brief in Opposition to ACS' and BSC's Motion for Summary Judgment on Obviousness dated Sep. 24, 1998.
Order dated Mar. 31, 2000.
Schatz Deposition Testimony; May 15, 1996: 79-83, 89-92, 105-107 and 153-161.
Schatz Deposition Testimony; May 16, 1996: 555-564, 569-572.
Schatz Deposition Testimony; Jan. 8, 1998: 67-73, 108-110.
Schatz Deposition Testimony; July 14, 1998: 69-77, 108-112, 119-123.
Schatz Deposition Testimony; Jul. 12, 1999: 88-91, 132-135, 144-149, 218-223, 231-242.
Schatz Deposition Testimony; Jul. 13, 1999: 251-334, 339-345, 374-416.
Schatz Deposition Testimony; Jul. 14, 1999: 454-550.
Schatz Deposition Testimony; Jul. 15, 1999: 560-614.
Schatz Deposition Testimony; Dec. 2, 1999: 906-91 1, 928-942, 945-963, 976-978, 1029-1034, 1038-1042.
Palmaz Deposition Testimony, Nov. 5, 1991: 160-172.
Palmaz Deposition Testimony, Feb. 5, 1995: 710-727.
Palmaz Deposition Testimony, Jul. 16, 1998: 55-56; 81-82.
Palmaz Deposition Testimony, Jul. 28, 1999: 560-568, 570-579.
Palmaz Deposition Testimony, Jul. 29, 1999: 778-785.
Palmaz Deposition Testimony, Aug. 31, 1999: 1403-1452.
Palmaz Deposition Testimony, Sep. 2, 1999; 1953-1960.

Palmaz Deposition Testimony, Oct. 14, 1999; 2201-2209; 2275-2342; 2371-2411.
Palmaz Deposition Testimony, Oct. 15, 1999: 2424-2497; 2508-2589.
Palmaz Deposition Testimony, Oct. 16, 1999; 2853-2860.
Tobor Deposition Testimony, Jun. 17, 1999: 837-958.
Tobor Deposition Testimony, Jun. 18, 1999: 1095-1184.
Tobor Deposition Testimony, Dec. 1, 1999: 1217-1371.
Tobor Deposition Testimony, Dec. 2, 1999: 1398-1414; 1444-1508; 1532-1548.
Tobor Deposition Testimony, Dec. 3, 1999: 1652-1653; 1662-1672; 1683-1694.
Kula Deposition Testimony, Apr. 20, 1999: 268-169.
Kula Deposition Testimony, Nov. 16, 1999: 660-675; 680-694; 7-8-755; 774-821.
Kula Deposition Testimony, Nov. 18, 1999; 176-223.
Expert Report of Dr. Rodney S. Badger on Behalf of Medtronic AVE, Inc. (Jan. 31, 2000).
Expert Report of Dr. Joseph Bonn on Behalf of Medtronic AVE, Inc. (Jan. 31, 2000).
Deposition of Dr. Joseph Bonn dated Mar. 14, 2000.
Rebuttal Expert Report of Nigel Buller, B.Sc., M.B., F.R.C.P. (Mar. 2000).
Second Supplement Rebuttal Expert Report of Nigel Buller, B.Sc., M.B., F.R.C.P. (Aug. 17, 2004).
Rebuttal Expert Report of John M. Collins, PH.D. (Feb. 2000).
Expert Report of David C. Cumberland, M.D. (Jan. 24, 2000).
Expert Report of John T. Goolkasian (Feb. 2000).
Deposition of Richard R. Heuser, M.D. (Sep. 7, 2004).
Deposition of Henry R. Piehler (Sep. 10, 2004).
Deposition of Ronald J. Solar (Mar. 22, 2000).
Deposition of Ronald J. Solar (Mar. 23, 2000).
Deposition of Ronald J. Solar (Apr. 12, 2000).
Expert Report of Dr. Arina Van Breda on Behalf of Medtronic AVE, Inc. (Jan. 31, 2000).
Deposition of Anna Van Breda (Mar. 24, 2000).
Deposition of Arina Van Breda (Aug. 21, 2004).
Expert Report of John F. Witherspoon (Jan. 24, 2000).
Supplemental Expert Report of John F. Witherspoon (Oct. 27, 2000).
Deposition of John F. Witherspoon (Mar. 8, 2000).
Palmaz et al., Article: "Normal and Stenotic Renal Arteries: Experimental Balloon Expandable Intraluminal Stenting", Radiology, Sep. 1987. (AVE 84).
Julio C. Palmaz, Article: "Expandable vascular endoprosthesis." (AVE 132).
Duprat et. al., Article: Flexible Balloon-Expandable Stent for Small Vessels Duprat et. al. Radiology, vol. 162, pp. 276-278, 1987. (AVE 134).
Coons et. al., Article: "Large-Bore, Long Biliary Endoprosthesis (Biliary Stents) for Improved Drainage," Radiology, vol. 148, pp. 89-94, 1983. (AVE 143).
Honickman et al., Article: "Malpositioned Biliary Endoprostesis, Technical Developments And Instrumentation," vol. 144, No. 2., 1982. (AVE 144).
Harries-Jones, et al., Article: "Repositioning of Biliary Endoprosthesis with Gruntzig Balloon Catheters," AJR, vol. 138, pp. 771-772, 1982. (AVE 153).
Charnsangavej et al., Article "Stenosis of the Vena Cava: Preliminary Assessment of Treatment with Expandable Metallic Stents," Radiology, vol. 161, pp. 295-298, 1986. (AVE 359).
Wallace, M. J. et al., Article "Tracheobronchial Tree: Expandable Metallic Stents Used in Experimental and Clinical Applications," Radiology, vol. 158, pp. 309-312, 1986. (AVE 364).
T. Yoshioka, et al., AIR Article: "Self-Expanding Endovascular Graft: An Experimental Study in Dogs", vol. 151, pp. 673-676, 1988. (AVE 438).
Palmaz, J. C. et al., Article: "Expandable Intraluminal Vascular Graft: A Feasibility Study," Surgery, vol. 99, pp. 199-205, 1986. (AVE 461).
Lawrence et al., Article: "Percutaneous Endovescular Graft: Experimental Evaluation." Radiology, vol. 163, pp. 357-360, 1987. (AVE 671).

Palmaz et al., Article: Expandable Intraluminal Graft: A Preliminary Study, Nov. 17-22, 1985, Radiology, vol. 156, pp. 73-77, 1985. (AVE 1224).
Fallone et al., "Elastic Characteristics of the Self-Expanding Metallic Stents," Investigative Radiology, vol. 23, pp. 370-376, 1988. (AVE 1953).
Palmaz Paper Entitled "Research Project Expandable Vascular Endoprosthesis" May 18, 1983.
Rousseau , et al., Publication: "Percutaneous Vascular Stent: Experimental Studies & Preliminary Clinical Results in Peripheral Arterial Diseases," in Inter. Angio, vol. 6, 153-161, 1987. (AVE 3301).
Rousseau , et al., Publication: "Self-Expanding Endovascular Prostesis; An Experimental Study," Radiology, vol. 164, pp. 709-714, 1987. (AVE 3303).
Wallace, et al., Article: "Tracheobronchial Tree: Expandable Metallic Stents Used in Experimental and Clinical Applications," Radiology, vol. 58, pp. 309-312, 1986. (DBX 2938).
Palmaz et al., Article: "Expandable Intraluminal Graft: A Preliminary Study," Radiology, vol. 156, pp. 73-77, Nov. 17-22, 1985 (DBX 4595).
Program for the 12th Annual Course on Diagnostic Angiography and Interventional Radiology Mar. 23-26, 1987 sponsored by the Society of Cardiovascular and Interventional Radiology (DBX 6235).
Preliminary Motion for Judgment re: Wolff claims 1, 2-8, 10, 15 and 19 (DBX6759).
Palmaz Declaration (DBX 7069).
Letter from Gaterud to Dr. R. Palmaz dated Jul. 5, 1988 with attached document entitled: "Segmented, balloon-expandable stents." (DBX 7160).
Duprat et al., Article: "Flexible Balloon-Expandable Stent For Small Vessels," Radiology, vol. 168, pp. 276-278, 1987 (PX 82).
Drawing Sent to Bodic on Mar. 17, 1986 (PX 374).
Letter from Dr. Palmaz to R. Bowman enclosing a model of the flexible coronary graft dated Mar. 17, 1986 (PX 337).
Lab Notebook pages dated Jul. 30, 1987 from Rodney Wolff (Cor 185596-597) (PX621A).
Charnsangavej, et al., Article: "Stenosis of The Vena Cava Preliminary Assessment of Treatment with expandable Metallic Stents," Radiology, vol. 161, No. 2, pp. 295-298 with attached photographs, 1986. (API 72).
J. Palmaz: The Current Status of Vascular Prostheses, published by SCIR in the Twelfth Annual Course on Diagnostic Angiography And Interventional Radiology Mar. 23-26, 1987. (API 73).
Amendment in Response to Office Action of Oct. 18, 1998 in re: Application of Julio Palmaz S/N 174,246. (API 152).
Article: Wallace, et al., Tracheobronchial Tree: Expandable Metallic Stents Used in Experimental and Clinical Applications Work In Progress, Radiology, vol. 158, pp. 309-312. (API 295).
Reply of Senior Party Schatz To Patentee Wolffs Opposition To The Belated Motion For Judgment Of Applicant Schatz With Regard To Wolff Claims 1, 2-8, 10, 1 1, 13-17, And 19 (COR 186450-455) (API 310).
Brief Of Senior Party Schatz At Final Hearing (API 313).
Letter from Ron Sickles to Ben Tobor dated Feb. 10, 1988 (Exhibit 42).
Letter from R.O. Sickles to Mike Tatlow dated May 12, 1988 (Exhibit 43).
Letter from R. O. Sickles to Richard Schatz dated Jun. 2, 1988 (Exhibit 44).
Letter from Richard Schatz to Raimund Erbel dated Jun. 3, 1988 (Exhibit 45).
Letter from Richard Schatz to Mike Schuler dated Aug. 29, 1991 (Exhibit 48).
Minutes of J&J Stent Project Review Meeting dated Jan. 21, 1988 (Exhibit 7).
Preliminary Motion for Judgment with Regard to Wolff Claims 1, 2-8, 10, 11, 13-17, and 19. (Exhibit 67).
Declaration of Richard A Schatz. (Exhibit 75).
Belated Motion for Judgement with Regard to Wolff Claims 1, 2-8, 10, 1 1, 13-17 and 19. (Schatz—Exhibit 77).
Letter from Dr. Schatz to Mr. Tobor, dated Jun. 3, 1988. (Exhibit 122).

Letter from Dr. Schatz to Mr. Romano, dated Nov. 28, 1988. (Exhibit 131).
Letter from Mr. Sickles to Mr. Tobor, dated Feb. 10, 1988 (Exhibit 145).
Richard A. Schatz, Article titled: "A View of Vascular Stents" Circulation, vol. 79, No. 2, pp. 445-457, 1989. (Exhibit 194).
Senior Party Schatz's reply to Patentee Wolff's Opposition to the Preliminary Motion Of Applicant Schatz for judgment with regard to Wolff Claims 1, 2-8, 10, 1 1, and 13-17. (Exhibit 69).
Wallace, et al., Article: "Tracheobronchial Tree: Expandable Metallic Stents Used in Experimental and Clinical Applications' Work In Progress," Radiology, vol. 158, pp. 309-312, 1986. (Exhibit 165).
Charnsangavej, et al., Article: "Stenosis of The Vena Cava Preliminary Assessment of Treatment with expandable Metallic Stents," Radioloby, vol. 161, No. 2, pp. 295-298 with attached photographs, 1986! (Exhibit 167).
David D. Lawrence et al., Publication: Percutaneous Endoyascular Graft: Experimental Evaluation[1], Radiology pp. 163, 357-360, 1987. (Exhibit 173).
Charles E. Putnam, M.D., Cover and article from "Investigative Radiology", vol. 23. No. 5, May 1988. (Exhibit 177).
Robert N. Berk, Cover and article from "American Journal of Roentology", pp. 673-676, 1988. (Exhibit 178).
Declaration of John S. Kula Under 37 CFR § 1 .672. ( Kula—Exhibit 77).
Yoshioka et al., Article: "Self-Expanding Endovascular Graft: An Experimental Study in Dogs" AJR, vol. 151, pp. 673-676, 1988. (PX 100).
Palmaz, et al., Article: Expandable Intraluminal Graft: A Preliminary Study Work in Progress[1], Radiology, vol. 156, No. 1, pp. 73-77, 1985. (PX 101).
Declaration of Richard Schatz Under 37 C.F.R. § 1.672. (PX 106).
Charnsangavej et al., Article: "Stenosis of the Vena Cave: Preliminary Assessment of Treatment with Expandable Metallic Stents," Radiology, vol. 161, pp. 295-298, 1986. (PX 143).
Wallace, et al., Article: Tracheobronchial Tree: Expandable Metallic Stents Used in Experimental and Clinical Applications Work in Progress[1], Radiology, vol. 158, pp. 309-312, 1986. (PX 144).
Gina Kolata, News Article: NY Times, "Devices That Opens Clogged Arteries Gets a Falling Grade in a New Study", pp. 16-18, Jan. 3, 1991. (PX 186).
Duprat, et al., Article: "Flexible Balloon—Expanded Stent for Small Vessels Work in Progress[1]", Radiology, vol. 62, pp. 276-278, 1987. (PX 207).
Letter from Palmaz to Bowman dated Mar. 17, 1986. (PX 350).
Memo re: Minutes of Stent Project Review—San Antonia—Mar. 15, 1988. (PX 651).
Kuntz, et al., Article: Clinical Cardiology Frontiers: "Defining Coronary Restenosis, Newer Clinical and Angiographic Paradigms", Circulation, Sep. 1993, vol. 88, No. 3, pp. 1310-1323. (PX 854).
Belated Motion for Judgment with regard to Wolff Claims1, 2-8, 10, 11, 13-17, and 19. (PX 1410).
Drawing of Sprial Stent (sent to Bodic Mar. 17, 1986). (PX2933).
Wright et al., Article: "Percutaneous Endovascular Stents: An Experimental Evaluation," Radiology, vol. 156, pp. 69-72, 1985. (PX 3093).
Charnsangavej et al., Article: "A New Expandable Metallic Stent for Dilation of Stenotic Tubular Structures: Experimental and Clinical Evaluation," Houston Medical Journal, vol. 3, pp. 41-51, Jun. 1987. (PX 3207).
In re Application of Wiktor, Appln. No. 69,636, Response to Office Action dated Mar. 17, 1988. (PX3236).
Transmittal Letter of Response to First Office Action in '417 patent. (PX 3993).
Letter from B. Tobor to R. Schatz dated Jul. 23, 1991. (PX 3996).
Mullins et al., Article: "Implantation of balloon—expandable intravascular grafts by catherization in pulmonary arteries and systemic veins," Circulation, vol. 77, No. 1, pp. 188-189, 1988. (PX4049).
Schatz et al., Article: "Intravascular Stents for Angioplasty," Cardio, 1997. (PX 4050).

Schatz et al., Article: "New Technology in Angioplasty Balloon—Expandable Intravascular Stents, New Developments in Medicine," vol. 2, No. 2 pp. 59-75, 1987. (PX4051).
Richard A. Schatz, Article: "Introduction to Intravascular Stents," Cardiology Clinics, vol. 6, No. 3, pp. 357-372, 1988. (PX 4052).
Richard A. Schatz, Article: "A View of Vascular Stents," Circulation, vol. 79, No. 2, pp. 445-457, 1989. (PX4053).
Wang et al., Article: "An Update on Coronary Stents," Cardio, pp. 177-186, 1992. (PX 4054).
Richard A. Schatz, Article: "New Technology in Angioplasty: Balloon-Expandable Starts," Medicamundi, vol. 33, No. 3, pp. 1 12-1 16, 1988. (PX 4055).
Letter from Tobor to Schatz dated Sep. 29, 1988. (PX1395).
Verified Statement of Facts by Unnamed Inventor R.A. Schatz document filed in U.S. Patent and Trademark Office on Sep. 8, 1989. (PX 3677).
Declaration of John S. Kula Under 37 CFR § 1.672 (Exhibit 329).
Letter to Mike Schular from R.A. Schatz dated Aug. 29, 1991. (Exhibit 402).
Articulated, Balloon—Expandable Stents, (DBX 7159).
J. Rosch et al., Experimental Intrahepatic Portacaval Anastomosis: Use of Expandable Gianturco Stents, Radiology, vol. 162, pp. 481-485, 1987.
J. Rosch et al., Modified Gianturco Expandable Wire Stents In Experimental and Clinical Use, Ann Radiol, vol. 31, No. 2, pp. 100-103, 1987.
J. Rosch et al., Gianturco Expandable Stents In the Treatment of Superior Vena Cava Syndrome Recurring After Vena Cava Syndrome Recurring After Maximum-Tolerance Radiation, Cancer, vol. 60, pp. 1243-1246, 1987.
I.E. Gordon, Structures or Why Things Don't Fall Down, Penguin Books, pp. 45-59, 132-148, 210-244,377-383.
Maass et al., Radiological Follow-up of Transluminally Inserted Vascular Endoprostheses: An Experimental Study Using Expanding Spirals, Radiology, vol. 152, pp. 659-663, 1984.
Argument submitted re EP 861 15473 dated Jan. 20, 1995. (AVE 2478).
Verified Statement of Facts by Julio C. Palmaz dated Aug. 4, 1989. (PX 3662).
Papanicolaou et al., Insertion of a Biliary Endoprosthesis Using A Balloon Dilatation Catheter, Gastrointest Radiology, vol. 10, pp. 394-396, 1985.
Palmaz et al., Atheroscierotic Rabbit Aortas; Expandable Intraluminal Grafting, Radiology, vol. 168, pp. 723-726, 1986.
Palmaz, The Current Status of Vascular Prostheses; Rosch et al., Gianturco, Expandable Stents in Experimental and Clinical Use, SCIVR, pp. 1 18-124, 1987.
Rosch et al., Abstract: Modified Gianturco Expandable Wire Stents in Experimental and Clinical Use, CIRSE, Porto Cervo, Sardinia, May 25-29, 1987.
Rosch et al., Gianturco Expandable Wire Stents in the Treatment of Superior Vena Cava Syndrome Recurring After Maximum-Tolerance Radiation, Cancer, vol. 60, pp. 1243-1246, 1987.
Mirich et al., Percutaneously Placed Endovascular Grafts for Aortic Aneurysms: Feasibility Study, Radiology, vol. 170, pp. 1033-1037, 1989.
Dotter, Transluminally-placed Coilspring Endarterial Tube Grafts, Investigative Radiology, vol. 4, Sep.-Oct., pp. 329-332, 1969.
Palmaz et al., Abstract: Expandable Intraluminal Graft: A Preliminary Study, Radiology, vol. 153 (P), Nov. 1983: 70th Scientific Assembly and Annual Meeting.
Cragg et al, Nonsurgical Placement of Arterial Endoprostheses: A New Technique Using Nitinol Wire, Radiology, vol. 147, pp. 261-263, Apr. 1983.
J. Rosch et al., Gianturco Expandable Stents in Experimental and Clinical Use, Program: "Twelfth Annual Course on Diagnostic Angiography and Interventional Radiology" (Society of Cardiovascular and Interventional Radiology, Pittsburgh, PA), Mar. 23-26, 1987 (the second Monofilament Article).
Uchida et al., Modifications of Gianturco Expandable Wire Stents, AIR, vol. 150, pp. 1185-1187, 1988.
Palmaz, Balloon-Expandable Intravascular Stent, AJR, vol. 1510, pp. 1263-1269.

*Cordis Corporation* v. *Advanced Cardiovascular Systems, Inc., Guidant Corporation, Arterial Vascular Engineering, Inc., Boston Scientific Corporation and SCMED Life Systems, Inc.*, Plaintiffs Complaint, Oct. 23, 1997 (Case No. 97-550-SLR).
*Arterial Vascular Engineering, Inc.* v. *Cordis Corporation, Johnson & Johnson and Expandable-Grafts Partnership*, Plaintiffs First Amended Complaint for Declaratory Relief of Patent Validity, Unenforceability, Noninfiingement, and for Antitrust Violations, Jan. 27, 1998 (Civil Action No. 97-700).
*Arterial Vascular Engineering, Inc.* v. *Cordis Corporation, Johnson & Johnson and Expandable-Grafts Partnership*, Cordis Corporation and Johnson & Johnson's Answer and Counterclaim, Feb. 27, 1998 (Civil Action No. 97-700-SLR).
*Arterial Vascular Engineering, Inc.* v. *Cordis Corporation, Johnson & Johnson and Expandable-Grafts Partnership*, Expandable-Graft Partnership's Answer, Feb. 27, 1998 (Civil Action No. 97-700-SLR).
*Arterial Vascular Engineering, Inc.* v. *Cordis Corporation, Johnson & Johnson and Expandable-Grafts Partnership*, Reply of Plaintiff Arterial Vascular Engineering, Inc. To Counterclaims of Defendant Cordis Corporation, Mar. 31, 1998 (Civil Action No. 97-700-SLR).
*Arterial Vascular Engineering, Inc.* v. *Cordis Corporation, Johnson & Johnson and Expandable-Grafts Partnership*, Reply of Plaintiff Arterial Vascular Engineering, Inc. To Counterclaims of Defendant Expandable Grafts Partnership, Mar. 31, 1998 (Civil Action No. 97-700-SLR).
*Cordis Corporation* v. *Advanced Cardiovascular Systems, Inc. and Guidant Corporation*, Cordis Corporation's Motion for a Preliminary Injunction, Oct. 8, 1997 (Civil Action No. 97-550).
*Cordis Corporation* v. *Advanced Cardiovascular Systems, Inc., Guidant Corporation Arterial Vascular Engineering, Inc., Boston Scientific Corporation and SCJJVIED, Inc.*, Cordis 's Motion for Preliminary Injuction Against Arterial Vascular Engineering, Inc., Dec. 29, 1997 (Case No. 97-550-SLR).
Deposition of R. Schatz, M.D. in *Cordis Corporation* v. *Advanced Cardiovascular Systems, Inc.*, taken on Jan. 8, 1998 (Civil Action No. 97-550 SLR).
Deposition of Lee P. Bendel in *Cordis Corporation* v. *Advanced Cardiovascular Systems, Inc.*, taken on Jan. 22, 1998 (Civil Action No. 97-550 SLR).
Deposition of Julio Cesar Palmaz in *Cordis Corporation* v. *Advanced Cardiovascular Systems, Inc.*, taken on Dec. 29, 1997 (Civil Action No. 97-550 SLR).
Deposition of Richard A. Bowman in *Cordis Corporation* v. *Advanced Cardiovascular Systems, Inc.*, taken on Jan. 9, 1998 (Civil Action No. 97-550 SLR).
Deposition of Gary Schneiderman in *Cordis Corporation* v. *Advanced Cardiovascular Systems, Inc.*, taken on Jan. 16, 1998 (Civil Action No. 97-550 SLR).
Deposition of David Pearle, M.D. in *Cordis Corporation* v. *Advanced Cardiovascular Systems, Inc.*, taken on Jul. 10, 1998 (Civil Action No. 97-550 SLR).
Preliminary Injuction hearing testimony taken on Feb. 9-13, 1998 (Civil Action No. 97-550 SLR).
*Cordis Corporation* v. *Advanced Cardiovascular Systems, Inc., et al.*, (Civil Action No. 97-550 SLR) and *Cordis Corporation* v. *Advanced Cardiovascular Systems, Inc. Et al.* (Civil Action No. 98-65-SLR), Opening Post Hearing Brief of Plaintiff Cordis Corporation in Support of Motion for Preliminary Injuction, Mar. 6, 1998 (Portions relevant to patent claim construction and patent validity issues).
*Cordis Corporation and Expandable Grafts Partnership* v. *Advanced Cardiovascular Systems, Inc. et al.*, Post-Hearing Reply Brief of Plaintiff Cordis Corporation in Support of Its Motion for Preliminary Injuction, Apr. 10, 1998 (Case No. 97-550 SLR) (Portions relevant to patent validity issues).
*Cordis Corporation and Expandable Grafts Partnership* v. *Advanced Cardiovascular Systems, Inc. et al.*, Plaintiffs Motion for a Preliminary Injuction Against Boston Scientific Corporation and SCLMED Life Systems, Inc. And Memorandum in Support, Apr. 13, 1998 (Case No. 97-550-SLR).
*Cordis Corporation and Expandable Grafts Partnership* v. *Advanced Cardiovascular Systems, Inc., et al.*, Judge Robinson's Order Denying Plaintiffs Motion for a Preliminary Injunction, Jul. 17, 1998 (Civil Action No. 97-550 SLR).
*Cordis Corporation and Expandable Grafts Partnership* v. *Advanced Cardiovascular Systems, Inc., et al.*, Defendant Boston Scientific Corporation and SCTMED Life Systems, Inc.'s Motion for Summary Judgment of Invalidity of U.S. Patent No. 5,102,417, Aug. 27, 1998 (Civil Action No. 97-550-SLR).
*Boston Scientific Limited, et al.* v. *Expandable Grafts Partnership*, Plaintiffs' Statement of Claim, Mar. 13, 1997 (UK Action No. 1493).
*Boston Scientific Limited, et al.* v. *Expandable Grafts Partnership*, Defendant's Amended Defense and Counterclaim, Aug. 14, 1997 (UK Action No. 1493).
*Boston Scientific Limited, et al.* v. *Expandable Grafts Partnership*, Petition for Revocation, Mar. 13, 1997 (UK Action No. 1497).
*Boston Scientific Limited, et al.* v. *Expandable Grafts Partnership*, Particulars of Objections, Mar. 13, 1997 (UK Action No. 1497).
*Boston Scientific Limited, et al.* v. *Expandable Grafts Partnership and Boston Scientific Limted et al.*, v. *Julio C. Palmaz*, Boston's Skeleton Argument (UK Action Nos. 1493, 1495, 1496, and 1497).
*Boston Scientific Limited, et al.* v. *Julio C. Palmaz and Expandable Grafts Partnership*, Skeleton Argument of Palmaz/EGP, Mar. 19, 1998 (UK Action Nos. 1493, 1495, 1496 and 1497).
*Boston Scientific Limited, et al.* v. *Julio C. Palmaz and Expandable Grafts Partnership*, EGP's Final Submissions, Apr. 2, 1998 (UK Action Nos. 1493, 1495, 1496 and 1497).
*Boston Scientific Limited, et al.* v. *Julio C. Palmaz and Expandable Grafts Partnership*, Judgment, Jun. 26, 1998 (UK Action Nos. 1493, 1495, 1496 and 1497).
Rosch, Modified Gianturco Expandable Wire Stents in Experimental and Clinical Use, CJJR.SE 1987 Presentation: see Witness Statement of Josef Rosch from U.K. Proceeding.
Statement of Claim By Boston Scientific et al. against *Expandable Grafts Partnership et al.*, in *EPG et al.*, v. *Boston Scientific et al.* in Netherlands (Mar. 13, 1997).
Motion for Joinder of Actions, Change of Claim and Statement of Claim filed by Expandable Grafts Partnership et al. in *EPG et al.* v. *Boston Scientific et al.* In Netherlands (Apr. 22, 1997).
Opinion of K.J. Merman filed in *EPG et al.* v. *Boston Scientific et al.* in Netherlands (Aug. 29, 1997).
Expert report of Dr. Nigel Buller in *EPG et al.* v. *Boston Scientific et al.* in Netherlands (Aug. 28, 1997).
Expert report of Lee P. Bendel in *EPG et al.* v. *Boston Scientific et al.* in Netherlands (Aug. 28, 1997).
Memorandum of Oral Pleading in *EPG et al.* v. *Boston Scientific et al.* in Netherlands (Sep. 12, 1997).
Plea Notes of P. A.M. in *EPG et al.* v. *Boston Scientific et al.* in Netherlands (Mar. 10, 1998).
Decision of Court of Appeals in *EPG et al.* v. *Boston Scientific et al.* in Netherlands (Apr. 23, 1998).
Translation of Nullity Action Against EPO 0 364 787 by Biotronik in Germany.
Translation of Nullity Action Against EPO 0 335 341 by Biotronik in Germany.
Translation of EPG Response to Nullity Action Against EP 0 364 787 by Biotronik in Germany.
Translation of EPG Response to Nullity Action EP 0 335 341 by Biotronik in Germany.
Nullity Suit Against EP-B1-0 335 341 Brought by Boston Scientific in Germany.
Translation of Opposition filed by Terumo Corp. Against Japan Patent No. 2680901.
Translation of Decision on Opposition Against Japan Patent No. 2680901.
Memorandum Order of the Court dated Sep. 7, 2000, concerning disputed claim constuction.
Translation of Judgment in Nullity Action Against EP 0 364 787 by Biotronik in Germany.
Translaion of Judgment in Nullity Action Against EP 0 335 341 by Biotronik in Germany.
Trial transcript from Mar. 17, 2005 at 171-172, 191-192.
Trial transcript from Mar. 18, 2005 at 282-285, 325-327, 349-351.
Trial transcript from Mar. 21, 2005 at 721-726.

Trial transcript from Mar. 24, 2005 at 1387.
Trial transcript from Jul. 26, 2005.
BSC's Opening Brief in Support of Its Motion for Judgment as a Matter of Law or, in the Alternative, for a New Trial, dated Mar. 16, 2001.
Cordis' Answering Brief in Opposition to BSC's Motion for JMOL or a New Trial on the Palmaz '762 Patent and the Schatz '332 Patents, dated Apr. 17, 2001.
BSC's Reply Brief in Support of Its Motion for Judgment as a Matter of Law or, in the Alternative, for a New Trial, dated May 11, 2001.
J. Rosch et al., Abstract, Expandable Gianturco-Type Wire Stents in Experimental Intrahepatic Portacaval Shunts, Program: "72nd Scientific Assembly and Annual Meeting of the Radiological Society of North America", Nov. 30-Dec. 5, 1986, Radiology, vol. 161, pp. 40-41, 1986.
*Cordis Corporation v. Boston Scientific*, Order Dated Mar. 27, 2006 (97-550-SLR).
*Cordis Corporation v. Boston Scientific*, Judgment in a Civil Case Dated Mar. 27, 2006 (97-550-SLR).
*Cordis Corporation v. Boston Scientific*, Memorandum Opinion Dated Mar. 27, 2006 (97-550-SLR).
*Cordis Corporation v. Boston Scientific*, Memorandum Opinion Dated Mar. 27, 2006 (97-550-SLR).
*Cordis Corporation v. Boston Scientific*, Memorandum Opinion Dated Mar. 27, 2006 (97-550-SLR).
*Cordis Corporation v. Boston Scientific*, Order Dated Mar. 27, 2006 (97-550-SLR).
*Cordis Corporation v. Boston Scientific*, Order Dated Mar. 27, 2006 (97-550-SLR).
*Cordis Corporation and Expandable Grafts Partnership v. Advanced Cardiovascular Systems, Inc., Guidant Corporation, Arterial Vascular Engineering, Inc., Boston Scientific Corporation and SCIMED Life Systems, Inc.*, Answer and Counterclaims of Defendant Advanced Cardiovascular Systems, Inc., Apr. 8, 1998 (Case No. 97-550-SLR).
*Boston Scientific Limited et al. v. Expandable Grafts Partnership and Boston Scientific Limited et al. v. Julio C. Palmaz*, Boston's Closing Submissions (UK Action Nos. 1493, 1495, 1496 and 1497).
*Cordis Corporation v. Advanced Cardiovascular Systems, Inc., Guidant Corporation, Arterial Vascular Engineering, Inc., Boston Scientific Corporation and SCIMED Life Systems, Inc.*, Defendants' Answer, Nov. 12, 1997 (Case No. 97-550-SLR).
Statement of Rejoinder in the Action on the Merits, Also Including an Amendment of Defendant's Final Position in the Principal Action, as Well as the Provisional Statement of Rejoinder in the Action on the Counterclaim in *EPG et al. v. Boston Scientific et al.* in Netherlands (Feb. 10, 1998).
Statement of Answer in the Ancillary Appeal in *EPG et al. v. Boston Scientific et al.* in Netherlands (Mar. 10, 1998).
Appeal filed by Expandable Grafts Partnership et al. in *EPG et al. v. Boston Scientific et al.* in Netherlands (Nov. 12, 1997).
Title filed by Boston Scientific et al. in *EPG et al. v. Boston Scientific et al.* in Netherlands (Jan. 22, 1998).
Deposition of Richard Schatz, M.D. in *Cordis Corporation v. Advanced Cardiovascular Systems, Inc.* taken on Jul. 14, 1998 (Civil Action No. 97-550-SLR).
Jury Verdict form from the *Cordis Corporation et al v. Boston Scientific Corporation, et al* liability trial, undated.
Trial testimony transcripts from the *Cordis Corporation et al. v. Boston Scientific Corporation et al.* liability trial dated Nov. 21, Nov. 27-Dec. 1, Dec. 4-8 and Dec. 11, 2000.
*Boston Scientific SCIMED, Inc. and Boston Scientific Corporation v. Cordis Corporation and Johnson and Johnson, Inc.*, Opening Expert Report of Stephen R. Hanson, Ph.D. (Civil Action No. 03-283-SLR).
*Boston Scientific SCIMED, Inc. and Boston Scientific Corporation v. Cordis Corporation and Johnson and Johnson, Inc.*, Opening Expert Report of Robson F. Storey, Ph.D. (Civil Action No. 03-283-SLR).
*Boston Scientific SCIMED, Inc. and Boston Scientific Corporation v. Cordis Corporation and Johnson and Johnson, Inc.*, Rebuttal Expert Report of Kinam Park, Ph.D. (Civil Action No. 03-283-SLR).
*Cordis Corporation v. Boston Scientific Corporation and SCIMED Life Systems, Inc.* (C.A. No. 03-027-SLR) and *Boston Scientific SCIMED, Inc., and Boston Scientific Corporation v. Cordis Corporation and Johnson and Johnson, Inc.* (C.A. No. 03-283-SLR) Combined Post-Hearing Brief In Support Of Cordis Corporation's Motion For Preliminary Injunction in C.A. No. 03-027-SLR, And In Opposition to Plaintiffs' Motion For Preliminary Injunction in C.A. No. 03-283-SLR.
*Cordis Corporation v. Boston Scientific Corporation and SCIMED Life Systems, Inc.* (C.A. No. 03-027-SLR) *Boston Scientific SCIMED, Inc., and Boston Scientific Corporation v. Cordis Corporation and Johnson and Johnson, Inc.* (C.A. No. 03-283-SLR), Boston Scientific's Opening Post-Hearing Brief.
*Cordis Corporation v. Boston Scientific Corporation and SCIMED Life Systems, Inc.* (C.A. No. 03-027-SLR) *Boston Scientific SCIMED, Inc., and Boston Scientific Corporation v. Cordis Corporation and Johnson and Johnson, Inc.* (C.A. No. 03-283-SLR), Combined Post-Hearing Answering Brief In Support of Cordis Corporation's Motion For Preliminary Injunction In C.A. No. 03-027-SLR, And In Opposition To Plaintiffs Motion For Preliminary Injunction in C.A. No. 03-283-SLR.
Wu et al., Silicone-covered self-expanding metallic stents for the palliation of malignant esophageal obstruction and esophagorespiratory fistulas: experience in 32 patients and a review of the literature, *Gastrointestinal Endoscopy*, 1994, pp. 22-33, vol. 40, No. 1, Portland Oregon.
Binmoeller, et al., Silicone-Covered Expandable Metallic Stents in the Esophagus: An Experimental Study, Endoscopy, 1992, pp. 416-420, vol. 24, Georg Thieme Verlag Stuttgart New York.
*Boston Scientific SCIMED, Inc., and Boston Scientific Corporation v. Cordis Corporation and Johnson and Johnson, Inc.*, Answering Memorandum in Opposition to Plantiffs Motion for a Preliminary Injunction and Appendix thereto (Civil Action No. 03-283-SLR).
*Boston Scientific SCIMED, Inc., and Boston Scientific Corporation v. Cordis Corporation and Johnson and Johnson, Inc.*, Plaintiff s Reply Brief in Support of Their Motion for Preliminary Injunction.
Rhine, Polymers for Sustained Macromolecule Release: Procedures to Fabricate Reproducible Delivery Systems and Control Release Kinetics, *Journal of Pharmaceutical Sciences*, 1 980, pp. 265-270, vol. 69, No. 3.
Langer et al., Controlled Release of Macromolecules From Polymers, *Biomedical Polymers Polymeric Materials and Pharmaceuticals for Biomedical Use*, 1980, pp. 112-137, Academic Press, Inc., New York, NY.
Langer et al., Applications of Polymeric Delivery Systems for Macromolecules and Factors Controlling Release Kinetics.
Rhine et al., A Method to Achieve Zero-Order Release Kinetics From Polymer Matric Drug Delivery Systems, pp. 67-72.
Langer et al., Polymers for the Sustained Release of Macromolecules: Controlled and Magnetically Modulated Systems, *Better Therapy With Existing Drugs: New Uses and Delivery Systems*; 1981, pp. 179-216, Merck Sharp & Dohme International, Rahway, NJ.
Hsieh, et al., Zero-Order Controlled-Release Polymer Matrices for Micro-and-Macromolecules, *Journal of Pharmaceutical Sciences* , 1983 pp. 17-22, vol. 72, No. 1.
Brown et al., In Vivo and In Vitro Release of Macromolecules from Polymeric Drug Delivery Systems, *Journal of Pharmaceutical Sciences*, 1983, pp. 1181-1185, vol. 72, No. 10.
Langer, Implantable Controlled Release Systems, *Pharmac. Ther.*, 1983, pp. 35-51, vol. 21, printed in Great Britain.
Kost et al., Controlled Release of Bioactive Agents, *Trends in Biotechnology*, 1984, pp. 47-51, vol. 2, No. 2, Elsevier BV Amsterdam.
Bawa et al., An Explanation for the Controlled Release of Macromolecules from Polymers, *Journal of Controlled Release*, 1985, pp. 259-267, vol. 1 Elsevier Science BV Amersterdam.
Leong et al., Polymeric controlled drug delivery, 1987, pp. 199-233, vol. 1/3, Elsevier Science Publishers BV Amsterdam.

Langer, Polymeric Delivery Systems, *Targeting of Drugs 2 Optimization Strategies*, 1989, pp. 165-174, Plenum Press, New York and London.
Langer, Biomaterials in Controlled Drug Delivery; New Perspectives from Biotechnological Advances; *Pharmaceutical Technology*, 1989, pp. 18, 23-24, 26, 28, 30.
Langer, Controlled Release Systems, pp. 115-124.
Laurencin et al., Polymeric Controlled Release Systems: New Methods for Drug Delivery, *Clinics in Laboratory Medicine*, 1987, pp. 301-323, vol. 7, No. 2, WB Saunders Company, Philadelphia.
Langer, Biopolymers in Controlled Release Systems, *Polymeric Biomaterials*, pp. 161-169.
Tsong-Pin Hsu et al., Polymers for the Controlled Release of Macromolecules: Effect of Molecular Weight of Ethylene-vinyl Acetate Copolymer, *Journal of Biomedical Materials Research*, 1985, pp. 445-460, vol. 19.
Langer, Polymers and Drug Delivery Systems, *Long-Acting Contraceptive Delivery Systems*, 1983, pp. 23-32, Harper & Row, Philadelphia, PA.
Langer, New Drug Delivery Systems: What the Clinician Can Expect, *Drug Therapy*, 1983, pp. 217-231.
Langer, et al., Chemical and Physical Structure of Polymers as Carriers for Controlled Release of Bioactive Agents: A Review, *Rev. Macromol. Chem. Phys.*, 1983, pp. 61-126.
Langer, Polymeric Delivery Systems for Controlled Drug Release, *Chem. Eng. Commun.* 1980, pp. 1-48-vol. 6, Gordon and Breach Science Publishers, Inc. USA.
Langer, et al., Biocompatibility of Polymeric Delivery Systems for Macomolecules, *Journal of Biomedical Materials Research*, 1981, pp. 267-277, vol. 15.
Langer, Controlled Release: A New Approach to Drug Delivery, *Technology Review*, 1981, pp. 26-34.
Langer, et al., Sustained Release of Macromolecules from Polymers, *Polymeric Delivery Systems*, pp. 175-176, Gordon and Breach Science Publishers, New York.
Langer, Polymers for the Sustained Release of Proteins and other Macromolecules, *Nature*, 1976, pp. 797, 263, 799-800, vol. 263, No. 5580.
Baker, et al., Controlled Release: Mechanisms and Rates (1974).
Hanson, et al., In Vivo Evaluation of Artificial Surfaces with a Nonhum Primate Model of Arterial Thrombosis,/ *Lab Clin. Med.*, Feb. 1980, pp. 289-304.
Baker, Controlled Release of Biologically Active Agents (1987) pp. 1-275.
*Cordis Corporation v. Boston Scientific Corporation* (CA. No. 03-27-SLR) and *Boston Scientific Scimed, Inc.*, v. *Cordis Corporation and Johnson & Johnson, Incorporated* (CA. No. 03-283-SLR) Hearing Transcripts for Jul. 21, 2003, Jul. 22, 2003, Jul. 23, 2003.
*Cordis Corporation v. Boston Scientific Corporation et al.* (CA. No. 03-027-SLR), and *Boston Scientific Scimed, Inc. et al.* v. *Cordis Corporation et al.* (CA. No. 03-283-SLR), Boston Scientific's Post-Hearing Reply Brief and Exhibits Thereto, Sep. 12, 2003.
*Cordis Corporation v. Boston Scientific Corporation et al.* (CA. No. 03-027-SLR), and *Boston Scientific Scimed, Inc. et al.* v. *Cordis Corporation et al.* (CA. 03-283-SLR), Memorandum Order, Nov. 21, 2003.
*Cordis Corporation v. Boston Scientific Corporation et al.* (CA. No. 03-027-SLR), and *Boston Scientific Scimed, Inc. et al.* v. *Cordis Corporation et al* (CA. No. 03-283-SLR), Deposition Transcript of Julio C. Palmaz.
*Arterial Vascular Engineering, Inc.* v. *Cordis Corporation, Johnson & Johnson and Expandable Grafts Partnership*, Cordis Corporation and Johnson & Johnson's Answer and Counterclaim, Feb. 27, 1998 (Civil Action No. 97-700-SLR).
Plea Notes in *EPG et al.* v. *Boston Scientific et al.* in Netherlands (Sep. 12, 1997).
Provisional Judgment *EPG et al.* v. *Boston Scientific et al.* in Netherlands (Oct. 29, 1997).
Trial testimony transcripts from the *Cordis Corporation et al.* v. *Medtronic AVE Inc., et al.* liability trial dated Nov. 6-9, 13-17 and 20-21, 2000.
Jury verdict form from the *Cordis Corporation et al.* v. *Medtronic AVE, Inc. et al.* liability trial.
Hearing testimony transript from the consolidated *Cordis Corporation et al.* v. *Medtronic AVE, Inc. et al. and Boston Scientific Corporation et al.* inequitable conduct hearing dated Feb. 7-9 and 12, 2001.
*Cordis Corporation v. Metronic Ave., Inc., et al*, OPINION, 97-550-SLR, dated Mar. 28, 2002.
*Cordis Corporation v. Advanced Cardiovascular Systems, Inc. et al.* (CA. No. 97-550-SLR), *Medtronic AVE, Inc.* v. *Cordis Corporation et al.* (CA. No. 97-700-SLR), *Boston Scientific Corporation* v. *Athicon, Inc. etal*(CA. No. 98-19-SLR), Expert Report of John T. Goolkasian, Esq.
*Cordis Corporation v. Advanced Cardiovascular Systems, Inc. et al.* (CA. No. 97-550-SLR), *Medtronic A VE, Inc.* v. *Cordis Corporation et al* (CA. No. 97-700-SLR), *Boston Scientific Corporation* v. *Athicon, Inc. et al* (CA. 98-19-SLR), Expert Report of John F. Witherspoon.

LOCAL DELIVERY OF RAPAMYCIN FOR TREATMENT OF PROLIFERATIVE SEQUELAE ASSOCIATED WITH PTCA PROCEDURES, INCLUDING DELIVERY USING A MODIFIED STENT

CROSS-REFERENCE TO RELATED APPLICATIONS

This application is a continuation of Ser. No. 10/951,385, filed Sep. 28, 2004, now pending, which is a continuation of Ser. No. 10/408,328, filed Apr. 7, 2003, now issued as U.S. Pat. No. 6,808,536, which is a continuation of application Ser. No. 09/874,117, filed Jun. 4, 2001, now issued as U.S. Pat. No. 6,585,764, which is a continuation of application Ser. No. 09/061,568, filed Apr. 16, 1998, now issued as U.S. Pat. No. 6,273,913, which in turn claims benefit of provisional application Ser. No. 60/044,692, filed Apr. 18, 1997. The disclosures of these prior applications are incorporated herein by reference in their entirety.

FIELD OF THE INVENTION

Delivery of rapamycin locally, particularly from an intravascular stent, directly from micropores in the stent body or mixed or bound to a polymer coating applied on stent, to inhibit neointimal tissue proliferation and thereby prevent restenosis. This invention also facilitates the performance of the stent in inhibiting restenosis.

BACKGROUND OF THE INVENTION

Re-narrowing (restenosis) of an artherosclerotic coronary artery after percutaneous transluminal coronary angioplasty (PTCA) occurs in 10–50% of patients undergoing this procedure and subsequently requires either further angioplasty or coronary artery bypass graft. While the exact hormonal and cellular processes promoting restenosis are still being determined, our present understanding is that the process of PTCA, besides opening the artherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3–6 months results in the filling in and narrowing of the vascular space sufficient to significantly obstruct coronary blood flow.

Several recent experimental approaches to preventing SMC proliferation have shown promise althrough the mechanisms for most agents employed are still unclear. Heparin is the best known and characterized agent causing inhibition of SMC proliferation both in vitro and in animal models of balloon angioplasty-mediated injury. The mechanism of SMC inhibition with heparin is still not known but may be due to any or all of the following: 1) reduced expression of the growth regulatory protooncogenes c-fos and c-myc, 2) reduced cellular production of tissue plasminogen activator; are 3) binding and dequestration of growth regulatory factors such as fibrovalent growth factor (FGF).

Other agents which have demonstrated the ability to reduce myointimal thickening in animal models of balloon vascular injury are angiopeptin (a somatostatin analog), calcium channel blockers, angiotensin converting enzyme inhibitors (captopril, cilazapril), cyclosporin A, trapidil (an antianginal, antiplatelet agent), terbinafine (antifungal), colchicine and taxol (antitubulin antiproliferatives), and c-myc and c-myb antinsense oligonucleotides.

Additionally, a goat antibody to the SMC mitogen platelet derived growth factor (PDGF) has been shown to be effective in reducing myointimal thickening in a rat model of balloon angioplasty injury, thereby implicating PDGF directly in the etiology of restenosis. Thus, while no therapy has as yet proven successful clinically in preventing restenosis after angioplasty, the in vivo experimental success of several agents known to inhibit SMC growth suggests that these agents as a class have the capacity to prevent clinical restenosis and deserve careful evaluation in humans.

Coronary heart disease is the major cause of death in men over the age of 40 and in women over the age of fifty in the western world. Most coronary artery-related deaths are due to atherosclerosis. Atherosclerotic lesions which limit or obstruct coronary blood flow are the major cause of ischemic heart disease related mortality and result in 500,000–600,000 deaths in the United States annually. To arrest the disease process and prevent the more advanced disease states in which the cardiac muscle itself is compromised, direct intervention has been employed via percutaneous transiuminal coronary angioplasty (PTCA) or coronary artery bypass graft (CABG) PTCA is a procedure in which a small balloon-tipped catheter is passed down a narrowed coronary artery and then expanded to re-open the artery. It is currently performed in approximately 250,000–300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute reocclusion) and in the long term (restenosis).

The mechanism of acute reocclusion appears to involve several factors and may result from vascular recoil with resultant closure of the artery and/or deposition of blood platelets along the damaged length of the newly opened blood vessel followed by formation of a fibrin/red blood cell thrombus. Recently, intravascular stents have been examined as a means of preventing acute reclosure after PTCA.

Restenosis (chronic reclosure) after angioplasty is a more gradual process than acute reocclusion: 30% of patients with subtotal lesions and 50% of patients with chronic total lesions will go on to restenosis after angioplasty. While the exact mechanism for restenosis is still under active investigation, the general aspects of the restenosis process have been identified.

In the normal arterial will, smooth muscle cells (SMC) proliferate at a low rate (<0.1%/day; ref). SMC in vessel wall exists in a contractile phenotype characterized by 80–90% of the cell cytoplasmic volume occupied with the contractile apparatus. Endoplasmic reticulum, golgi bodies, and free ribosomes are few and located in the perinuclear region. Extracellular matrix surrounds SMC and is rich in heparin-like glycosylaminoglycans which are believed to be responsible for maintaining SMC in the contractile phenotypic state.

Upon pressure expansion of an intracoronary balloon catheter during angioplasty, smooth muscle cells within the arterial wall become injured. Cell derived growth factors such as platelet derived growth factor (PDGF), basic fibroblast growth factor (bFGF), epidermal growth factor (EGF), etc. released from platelets (i.e., PDGF) adhering to the damaged arterial luminal surface, invading macrophages and/or leukocytes, or directly from SMC (i.e., BFGF) provoke a proliferation and migratory response in medial SMC. These cells undergo a phenotypic change from the contractile phenotyope to a synthetic phenotype characterized by only few contractile filament bundles but extensive rough endoplasmic reticulum, golgi and free ribosomes. Proliferation/migration usually begins within 1–2 days post-injury and peaks at 2 days in the media, rapidly declining thereafter (Campbell et al., In: Vascular Smooth Muscle Cells in Culture, Campbell, J. H. and Campbell, G. R., Eds, CRC Press, Boca. Ratioh, 1987, pp. 39–55); Clowes, A. W. and Schwartz, S. M., Circ. Res. 56:139–145, 1985).

Finally, daughter synthetic cells migrate to the intimal layer of arterial smooth muscle and continue to proliferate. Proliferation and migration continues until the damaged luminal endothelial layer regenerates at which time proliferation ceases within the intima, usually within 7–14 days postinjury. The remaining increase in intimal thickening which occurs over the next 3–6 months is due to an increase in extracellular matrix rather than cell number. Thus, SMC migration and proliferation is an acute response to vessel injury while intimal hyperplasia is a more chronic response. (Liu et al., Circulation, 79:1374–1387, 1989).

Patients with symptomatic reocclusion require either repeat PTCA or CABG. Because 30–50% of patients undergoing PTCA will experience restenosis, restenosis has clearly limited the success of PTCA as a therapeutic approach to coronary artery disease. Because SMC proliferation and migration are intimately involved with the pathophysiological response to arterial injury, prevention of SMC proliferation and migration represents a target for pharmacological intervention in the prevention of restenosis.

SUMMARY OF THE INVENTION

Novel Features and Applications to Stent Technology Currently, attempts to improve the clinical performance of stents have involved some variation of either applying a coating to the metal, attaching a covering or membrane, or embedding material on the surface via ion bombardment. A stent designed to include reservoirs is a new approach which offers several important advantages over existing technologies.

Local Drug Delivery from a Stent to Inhibit Restenosis

In this application, it is desired to deliver a therapeutic agent to the site of arterial injury. The conventional approach has been to incorporate the therapeutic agent into a polymer material which is then coated on the stent. The ideal coating material must be able to adhere strongly to the metal stent both before and after expansion, be capable of retaining the drug at a sufficient load level to obtain the required dose, be able to release the drug in a controlled way over a period of several weeks, and be as thin as possible so as to minimize the increase in profile. In addition, the coating material should not contribute to any adverse response by the body (i.e., should be non-thrombogenic, non-inflammatory, etc.). To date, the ideal coating material has not been developed for this application.

An alternative would be to design the stent to contain reservoirs which could be loaded with the drug. A coating or membrane of biocompatable material could be applied over the reservoirs which would control the diffusion of the drug from the reservoirs to the artery wall.

One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

BRIEF DESCRIPTION OF THE DRAWINGS

The invention will be better understood in connection with the following figures in which.

DETAILED DESCRIPTION OF ILLUSTRATIVE EMBODIMENTS

Pharmacological attempts to prevent restenosis by pharmacologic means have thus far been unsuccessful and all involve systemic administration of the trial agents. Neither aspirin-dipyridamole, ticlopidine, acute heparin administration, chronic warfarin (6 months) nor methylprednisolone have been effective in preventing restenosis although platelet inhibitors have been effective in preventing acute reocclusion after angioplasty. The calcium antagonists have also been unsuccessful in preventing restenosis, although they are still under study. Other agents currently under study include thromboxane inhibitors, prostacyclin mimetics, platelet membrane receptor blockers, thrombin inhibitors and angiotensin converting enzyme inhibitors. These agents must be given systemically, however, and attainment of a therapeutically effective dose may not be possible; antiproliferative (or anti-restenosis) concentrations may exceed the known toxic concentrations of these agents so that levels sufficient to produce smooth muscle inhibition may not be reached (Lang et al., 42 Ann. Rev. Med., 127–132 (1991); Popma et al., 84 Circulation, 1426–1436 (1991)).

Additional clinical trials in which the effectiveness for preventing restenosis of dietary fish oil supplements, thromboxane receptor antagonists, cholesterol lowering agents, and serotonin antagonists has been examined have shown either conflicting or negative results so that no pharmacological agents are as yet clinically available to prevent post-angioplasty restenosis (Franklin, S. M. and Faxon, D. P., 4 Coronary Artery Disease, 2-32-242 (1993); Serruys, P. W. et al., 88 Circulation, (part 1) 1588–1601, (1993).

Conversely, stents have proven useful in preventing reducing the proliferation of restenosis. Stents, such as the stent 10 seen in layout in FIG. 4, balloon-expandable slotted metal tubes (usually but not limited to stainless steel), which when expanded within the lumen of an angioplastied coronary artery, provide structural support to the arterial wall. This support is helpful in maintaining an open path for blood flow. In two randomized clinical trials, stents were shown to increase angiographic success after PTCA, increase the stenosed blood vessel lumen and to reduce the lesion recurrence at 6 months (Serruys et al., 331 New Eng Jour. Med, 495, (1994); Fischman et al., 331 New Eng Jour. Med, 496–501 (1994). Additionally, in a preliminary trial, heparin coated stents appear to possess the same benefit of reduction in stenosis diameter at follow-up as was observed with non-heparin coated stents. Additionally, heparin coating appears to have the added benefit of producing a reduction in sub-acute thrombosis after stent implantation (Serruys et al., 93 Circulation, 412–422, (1996). Thus, 1) sustained mechanical expansion of a stenosed coronary artery has been shown to provide some measure of restenosis prevention, and 2) coating of stents with heparin has demonstrated both the feasibility and the clinical usefulness of delivering drugs to local, injured tissue off the surface of the stent.

Numerous agents are being actively studied as antiproliferative agents for use in restenosis and have shown some activity in experimental animal models. These include: heparin and heparin fragments (Clowes and Karnovsky, 265 Nature, 25–626, (1977); Guyton, J. R. et al. 46 Circ. Res., 625–634, (1980); Clowes, A. W. and Clowes, M. M., 52 Lab. Invest., 611–616, (1985); Clowes, A. W. and Clowes, M. M., 58 Circ. Res., 839–845 (1986); Majesky et al., 61 Circ Res., 296–300, (1987); Snow et al., 137 Am. J. Pathol., 313–330 (1990); Okada, T. et al., 25 Neurosurgery, 92–898, (1989) colchicine (Currier, J. W. et al., 80 Circulation, 11–66, (1989), taxol (ref), agiotensin converting enzyme (ACE) inhibitors (Powell, J. S. et al., 245 Science, 186–188 (1989), angiopeptin (Lundergan, C. F. et al., 17 Am. J. Cardiol. (Suppi. B); 132B–136B (1991), Cyclosporin A (Jonasson, L. et. al., 85 Proc. Nati, Acad. Sci., 2303 (1988), goat-anti-rabbit PDGF antibody (Ferns, G. A. A., et al., 253 Science, 1129–1132 (1991), terbinafine (Nemecek, G. M. et al., 248 J. Pharmacol. Exp. Thera., 1167–11747 (1989), trapidil (Liu, M. W. et al., 81 Circulation, 1089-1093 (1990), interferon-gamma (Hansson, G. K. and Holm, 84 J. Circulation, 1266–1272 (1991), steroids (Colburn, M. D. et al., 15 J. Vasc. Surg., 510–518 (1992), see also Berk, B. C. et al., 17 J. Am. Coll. Cardiol., 111B–117B (1991), ionizing radiation (ref), fusion toxins (ref) antisense oligonucleotides (ref), gene vectors (ref), and rapamycin (see below).

Of particular interest in rapamycin. Rapamycin is a macrolide antibiotic which blocks IL-2-mediated T-cell proliferation and possesses antiinflammatory activity. While the precise mechanism of rapamycin is still under active investigation, rapamycin has been shown to prevent the $G_1$ to S phase progression of T-cells through the cell cycle by inhibiting specific cell cyclins and cyclin-dependent protein kinases (Siekierka, Immunol. Res. 13: 110–116, 1994). The antiproliferative action of rapamycin is not limited to T-cells; Marx et al. (Circ Res 76:412–417, 1995) have demonstrated that rapamycin prevents proliferation of both rat and human SMC in vitro while Poon et al. have shown the rat, porcine, and human SMC migratin can also be inhibited by rapamycin (J Clin Invest 98: 2277–2283, 1996). Thus, rapamycin is capable of inhibiting both the inflammatory response known to occur after arterial injury and stent implantation, as well as the SMC hyperproliferative response. In fact, the combined effects of rapamycin have been demonstrated to result in a diminished SMC hyperproliferative response in a rat femoral artery graft model and in both rat and porcine arterial balloon injury models (Gregory et al., Transplantation 55:1409–1418, 1993; Gallo et al., in press, (1997)). These observations clearly support the potential use of rapamycin in the clinical setting of post-angioplasty restenosis.

Although the ideal agent for restenosis has not yet been identified, some desired properties are clear: inhibition of local thrombosis without the risk systemic bleeding complications and continuous and prevention of the dequale of arterial injury, including local inflammation and sustained prevention smooth muscle proliferation at the site of angioplasty without serious systemic complications. Inasmuch as stents prevent at least a portion of the restenosis process, an agent which prevents inflammation and the proliferation of SMC combined with a stent may provide the most efficacious treatment for post-angioplasty restenosis.

Experiments

Agents: Rapamycin (sirolimus) structural analogs (macrocyclic lactones) and inhibitors of cell-cycle progression.

Delivery Methods: These can vary:
  Local delivery of such agents (rapamycin) from the struts of a stent, from a stent graft, grafts, stent cover or sheath.
  Involving comixture with polymers (both degradable and nondegrading) to hold the drug to the stent or graft.
  or entrapping the drug into the metal of the stent or graft body which has been modified to contain micropores or channels, as will be explained further herein.
  or including covalent binding of the drug to the stent via solution chemistry techniques (such as via the Carmeda process) or dry chemistry techniques (e.g. vapour deposition methods such as rf-plasma polymerization) and combinations thereof.
  Catheter delivery intravascularly from a tandem balloon or a porous balloon for intramural uptake.
  Extravascular delivery by the pericardial route.
  Extravascular delivery by the adventital application of sustained release formulations.

Uses:
  for inhibition of cell proliferation to prevent neointimal proliferation and restenosis.
  prevention of tumor expansion from stents.
  prevent ingrowth of tissue into catheters and shunts inducing their failure.

1. Experimental Stent Delivery Method—Delivery from Polymer Matrix:

Solution of Rapamycin, prepared in a solvent miscible with polymer carrier solution, is mixed with solution of polymer at final concentration range 0.001 weight % to 30 weight % of drug. Polymers are biocompatible (i.e., not elicit any negative tissue reaction or promote mural thrombus formation) and degradable, such as lactone-based polyesters or copolyesters, e.g., polylactide, polycaprolactonglycolide, polyorthoesters, polyanhydrides; poly-amino acids; polysaccharides; polyphosphazenes; poly(ether-ester) copolymers, e.g., PEO-PLLA, or blends thereof. Nonabsorbable biocompatible polymers are also suitable candidates. Polymers such as polydimethylsiolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters.

Polymer/drug mixture is applied to the surfaces of the stent by either dip-coating, or spray coating, or brush coating or dip/spin coating or combinations thereof, and the solvent allowed to evaporate to leave a film with entrapped rapamycin.

2. Experimental Stent Delivery Method—Delivery from Microporous Depots in Stent Through a Polymer Membrane Coating:

Stent, whose body has been modified to contain micropores or channels is dipped into a solution of Rapamycin, range 0.001 wt % to saturated, in organic solvent such as acetone or methylene chloride, for sufficient time to allow solution to permeate into the pores. (The dipping solution can also be compressed to improve the loading efficiency.) After solvent has been allowed to evaporate, the stent is dipped briefly in fresh solvent to remove excess surface bound drug. A solution of polymer, chosen from any identified in the first experimental method, is applied to the stent as detailed above. This outer layer of polymer will act as diffusion-controller for release of drug.

3. Experimental Stent Delivery Method—Delivery via Lysis of a Covalent Drug Tether:

Rapamycin is modified to contain a hydrolytically or enzymatically labile covalent bond for attaching to the surface of the stent which itself has been chemically derivatized to allow covalent immobilization. Covalent bonds such as ester, amides or anhydrides may be suitable for this.

4. Experimental Method—Pericardial Delivery:

A: Polymeric Sheet

Rapamycin is combined at concentration range previously highlighted, with a degradable polymer such as poly(caprolactone-gylcolid-e) or non-degradable polymer, e.g., polydimethylsiloxane, and mixture cast as a thin sheet, thickness range 10.mu. to 1000.mu. The resulting sheet can be wrapped perivascularly on the target vessel. Preference would be for the absorbable polymer.

B: Conformal Coating:

Rapamycin is combined with a polymer that has a melting temperature just above 37° C., range 40°–45° C. Mixture is applied in a molten state to the external side of the target vessel. Upon cooling to body temperature the mixture solidifies conformably to the vessel wall. Both non-degradable and absorbable biocompatible polymers are suitable.

Figure 1:
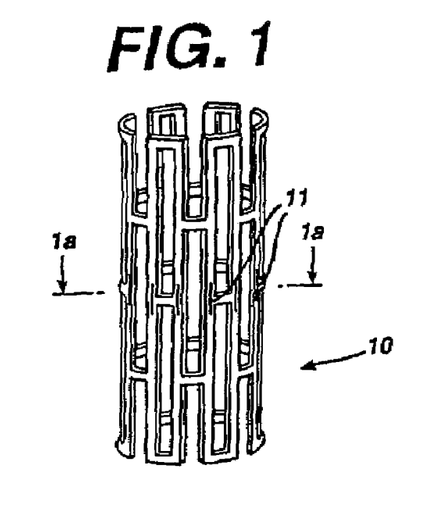
FIGS. 1 and 1A are top views and section views of a stent containing reservoirs as described in the present invention.
Figure 1A:
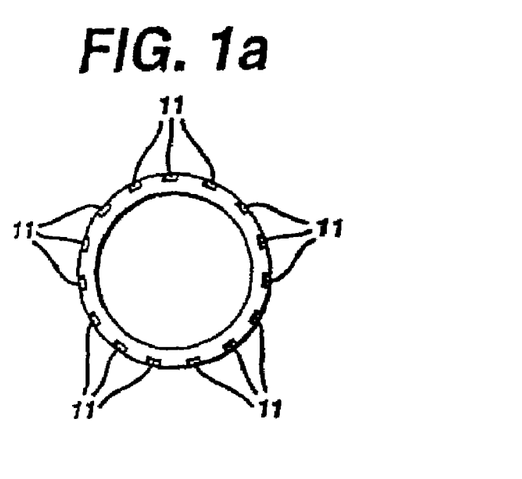
Figure 2A:
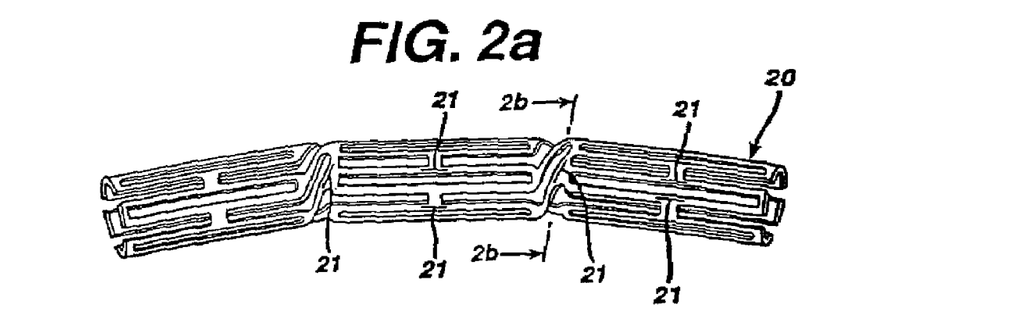
FIGS. 2a and 2b are similar views of an alternate embodiment of the stent with open ends.
Figure 2B:
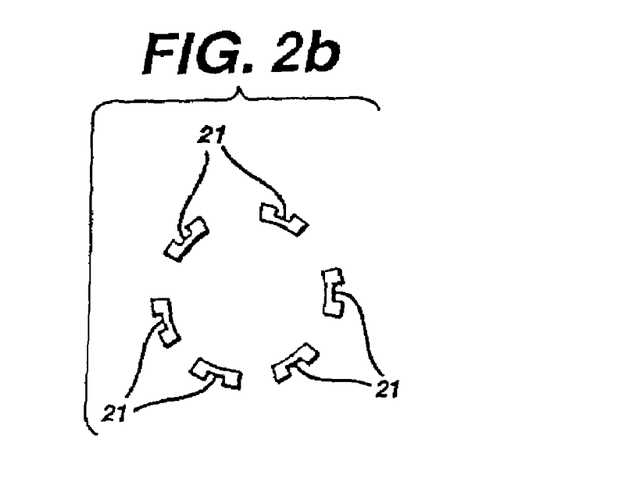
Figure 3A:
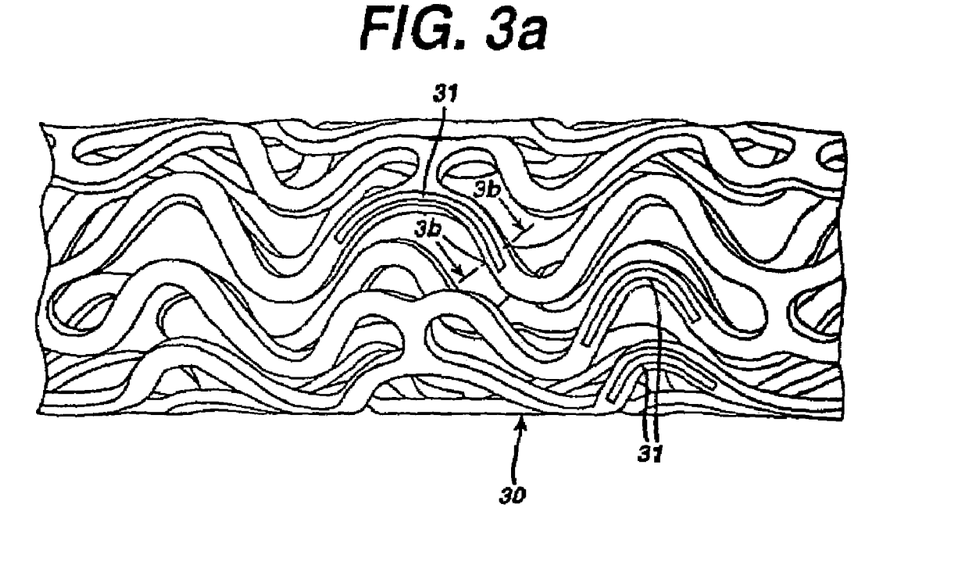
FIGS. 3a and 3b are further alternate figures of a device containing a grooved reservoir.
Figure 3B:
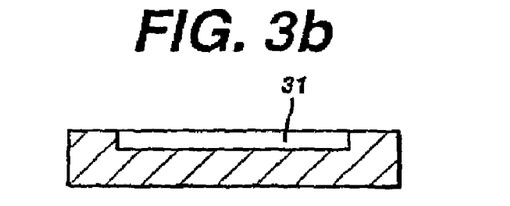
Figure 4:
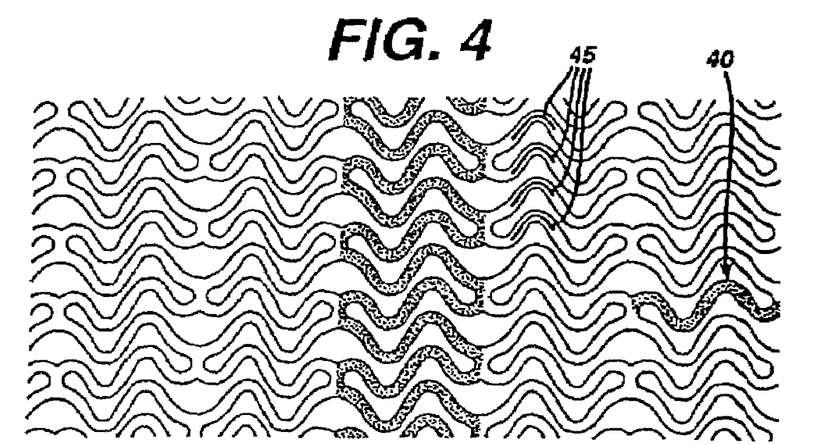
FIG. 4 is a layout view of a device containing a reservoir as in FIG. 3.

As seen in the figures it is also possible to modify currently manufactured stents in order to adequately provide the drug dosages such as rapamycin. As seen in FIGS. 1a, 2a and 3a, any stent strut 10, 20, 30 can be modified to have a certain reservoir or channel 11, 21, 31. Each of these reservoirs can be open or closed as desired. These reservoirs can hold the drug to be delivered. FIG. 4 shows a stent 40 with a reservoir 45 created at the apex of a flexible strut. Of course, this reservoir 45 is intended to be useful to deliver rapamycin or any other drug at a specific point of flexibility of the stent. Accordingly, this concept can be useful for "second generation" type stents.

In any of the foregoing devices, however, it is useful to have the drug dosage applied with enough specificity and enough concentration to provide an effective dosage in the lesion area. In this regard, the reservoir size in the stent struts must be kept at a size of about 0.0005" to about 0.003". Then, it should be possible to adequately apply the drug dosage at the desired location and in the desired amount.

These and other concepts will are disclosed herein. It would be apparent to the reader that modifications are possible to the stent or the drug dosage applied. In any event, however, the any obvious modifications should be perceived to fall within the scope of the invention which is to be realized from the attached claims and their equivalents.

What is claimed:

1. A metallic stent having a coating applied thereto, wherein:
    said coating comprises a mixture of a biocompatible polymeric carrier and a therapeutic agent;
    said polymeric carrier comprises at least one nonabsorbable polymer;
    said therapeutic agent is rapamycin, or a macrocyclic lactone analog thereof, present in an amount effective to inhibit neointimal proliferation; and
    said stent provides a controlled release of said therapeutic agent over a period of several weeks.

2. The metallic stent according to claim 1 wherein said therapeutic agent is a macrocyclic lactone analog of rapamycin.

3. The metallic stent according to claim 1 wherein said biocompatible polymeric carrier comprises a fluorinated polymer.

4. The metallic according to claim 3 wherein said biocompatible polymeric carrier further comprises an acrylate-based polymer or copolymer.

5. A method of inhibiting neointimal proliferation in a coronary artery resulting from percutaneous transluminal coronary angioplasty comprising implanting a metallic stent according to any one of claims 1 to 4 in the lumen of said coronary artery.

* * * * *

UNITED STATES PATENT AND TRADEMARK OFFICE
CERTIFICATE OF CORRECTION

PATENT NO. : 7,229,473 B2  Page 1 of 1
APPLICATION NO. : 11/466983
DATED : June 12, 2007
INVENTOR(S) : Robert Falotico et al.

It is certified that error appears in the above-identified patent and that said Letters Patent is hereby corrected as shown below:

Title Page,
Item (56), References Cited,
U.S. PATENT DOCUMENTS:
Page 2, "5,195,984 A" reference, delete "Schalz" and insert -- Schatz --.

OTHER PUBLICATIONS: Item [56]
Page 6, "Vasey, C. G. et al.," reference, delete "Flow", ," and insert -- Flow", --.
Page 8, "Belated Motion For Judgment" reference, delete "1 1," and insert -- 11, --.
Page 9, "Senior Party Schatz's reply" reference, delete "1 1," and insert -- 11, --.
Page 9, "Duprat, et al.," reference, delete "vol. 62," and insert -- vol. 162, --.
Page 9, "Belated Motion for Judgment" reference, delete "Wolff Claims1," and insert -- Wolff Claims 1, --.

Column 4,
Line 50, delete "preventing" and insert -- preventing and --.

Column 5,
Line 46, delete "migratin" and insert -- migration --.
Line 61, delete "risk systemic" and insert -- risk of systemic --.

Column 8,
Line 31, claim 4, delete "metallic according" and insert -- metallic stent according --.

Signed and Sealed this

Twenty-fourth Day of June, 2008

JON W. DUDAS
*Director of the United States Patent and Trademark Office*